US007169930B2

(12) United States Patent
Nicolaou et al.

(10) Patent No.: US 7,169,930 B2
(45) Date of Patent: *Jan. 30, 2007

(54) ANALOGS OF EPOTHILONE

(75) Inventors: Kyriacos C. Nicolaou, La Jolla, CA (US); Andreas Ritzen, Vanlose (DK); Kenji Namoto, Zurich (CH)

(73) Assignee: The Scripps Research Institute, La Jolla, CA (US)

( * ) Notice: Subject to any disclaimer, the term of this patent is extended or adjusted under 35 U.S.C. 154(b) by 13 days.

This patent is subject to a terminal disclaimer.

(21) Appl. No.: 10/634,537

(22) Filed: Aug. 4, 2003

(65) Prior Publication Data

US 2004/0072870 A1    Apr. 15, 2004

Related U.S. Application Data

(60) Provisional application No. 60/480,933, filed on Jun. 24, 2003, provisional application No. 60/400,535, filed on Aug. 2, 2002.

(51) Int. Cl.
C07D 417/06    (2006.01)
(52) U.S. Cl. ............. 548/182; 514/365; 514/369; 548/187; 548/202; 548/204
(58) Field of Classification Search ............. 548/187, 548/202, 204, 182; 514/365, 369
See application file for complete search history.

(56) References Cited

U.S. PATENT DOCUMENTS 6,531,497 B1 *    3/2003    Nicolaou et al. ............ 514/370

FOREIGN PATENT DOCUMENTS

| WO | WO-99/54318 A1 * | 10/1999 |
| WO | WO-99/67252 A2 * | 12/1999 |
| WO | WO-2003/026744 A1 * | 4/2003 |

OTHER PUBLICATIONS

Golub et al., Science, vol. 286, Oct. 15, 1999, pp. 531-537.*
Souto, et al., "New Fluorescent Water-Soluble Taxol Derivatives", *Angew. Chem. Int. Ed. Engl.* 34: 2710-2712 (1995).
Nicolaou, et al., "The Olefin Metathesis Approach to Epothilone A and Its Analogues", *J. Am. Chem. Soc.* 119: 7960-7973 (1997).
Nicolaou, et al., "Total Syntheses of Epothilones A and B via a Macrolactonization-Based Strategy", *J. Am. Chem. Soc.* 119: 7974-7991 (1997).

Nicolaou, et al., "Designed Epothilones: Combinatorial Synthesis, Tubulin Assembly Properties, and Cytotoxic Action against Taxol-Resistant Tumor Cells", *Angew. Chem. Int. Ed. Engl.* 36: 2097-2103 (1997).
Nicolaou, et al., "Total Synthesis of Epothilone E and Analogues with Modified Side Chains through the Stille Coupling Reaction", *Angew. Chem. Int. Ed. Engl.* 37: 84-87 (1998).
Nicolaou, et al., "Chemical Biology of Epothilones", *Angew. Chem. Int. Ed. Engl.* 37: 2015-2045 (1998).
Nicolaou, et al., "Total Synthesis of Epothilone E and Related Side-chain Modified Analogues via a Stille Coupling Based Strategy", *Bioorg. Med. Chem.* 7: 665-697 (1999).
Giannakakou, et al., "A common pharmacophore for epothilone and taxanes: Molecular basis for drug resistance conferred by tubulin mutations in human cancer cells", *Proc. Natl. Acad. Sci. USA* 97: 2904-2909 (2000).
Johnson, et al., "Synthesis, Structure Proof, and Biological Activity of Epothilone Cyclopropanes", *Org. Lett.* 2: 1537-1540(2000).
Nicolaou, et al., "Chemical synthesis and biological properties of pyridine epothilones", *Chem. Biol.* 7: 595-599 (2000).
Nicolaou, et al., "Total Synthesis of 16-Desmethylepothilone B, Epothilone $B_{10}$, Epothilone F, and Related Side Chain Modified Epothilone B Analogues", *Chem. Eur. J.* 6: 2783-2800 (2000).
Nicolaou, et al., " Synthesis and Biological Evaluation of 12,13-Cyclopropyl and 12,13-Cyclobutyl Epothilones", *ChemBioChem* 2: 69-75 (2001).
Sinha, et al., "Synthesis of Epothilone Analogues by Antibody-Catalyzed Resolution of Thiazole Aldol Synthons on a Multigram Scale. Biological Consequences of C-13 Alkylation of Epothilones", *ChemBioChem* 2: 656-665 (2001).
Nicolaou, et al., "Recent developments in the chemistry, biology and medicine of the epothilones", *Chem. Commun.*: 1523-1535 (Sep. 7, 2001), Issue 17.
Andreu, et al., "The Interaction of Baccatin III with the Taxol Binding Site of Microtubules Determined by a Homogenous Assay with Fluorescent Taxoid", *Biochemistry* 40: 11975-11984 (2001).
Nicolaou, et al., "Chemical Synthesis and Biogiccal Evaluation of cis- and trans-12,13-Cyclopropyl and 12,13-Cyclobutyl Epothilones and Related Pyridine Side Chain Analogues", *J. Am. Chem. Soc.* 123: 9313-9323 (2001).
Nicolaou, et al., "Chemical synthesis and biological evaluation of novel epothilone B and trans-12,13-cyclopropyl epothilone B analogues", *Tetrahedron* 58: 6413-6432 (Aug. 5, 2002).

* cited by examiner

*Primary Examiner*—Laura L. Stockton
(74) *Attorney, Agent, or Firm*—Donald G. Lewis

(57) ABSTRACT

Designed epoxide and cyclopropane epothilone analogs with substituted side-chains are disclosed and characterized with respect to their biological activities against a series of human cancer cell lines. Among the several bioactive analogs, the epothilone B analog with a thiomethyl thiazole ring stands out as the most potent.

5 Claims, 16 Drawing Sheets

| Compound | Cell Line | | | | | | | |
|---|---|---|---|---|---|---|---|---|
| | 1A9 | | A8 | | PTX10 | | PTX22 | |
| | $IC_{50}$ (nM) | | $IC_{50}$ (nM) | RR | $IC_{50}$ (nM) | RR | $IC_{50}$ (nM) | RR |
| Taxol[TM] | 3.0 ± 0.4 | | 10.1 ± 2.9 | 3.3 | 89.7 ± 9.0 | 29.5 | 53.4 ± 26.5 | 17.6 |
| Epo A | 2.4 ± 0.6 | | 91.0 ± 10.0 | 38.7 | 34.2 ± 2.0 | 14.5 | 8.7 ± 2.2 | 3.7 |
| Epo B | 0.6 ± 0.3 | | 6.5 ± 0.9 | 10.7 | 3.1 ± 0.5 | 5.2 | 0.8 ± 0.5 | 1.3 |
| 3 | 0.17 ± 0.8 | | 1.3 ± 0.65 | 7.6 | 0.26 ± 0.11 | 1.5 | 0.25 ± 0.17 | 1.5 |
| 104 | 0.1 ± 0.0 | | 2.4 ± 1.1 | 23.5 | 0.7 ± 0.3 | 6.5 | 0.6 ± 0.5 | 5.9 |
| 106 | 0.3 ± 0.1 | | 10.4 ± 2.4 | 41.4 | 3.3 ± 1.2 | 13.2 | 1.3 ± 1.1 | 5.3 |
| 108 | 3.5 ± 0.7 | | 18.4 ± 1.4 | 5.3 | 16.1 ± 2.1 | 4.6 | 3.8 ± 0.3 | 1.1 |
| 109 | 4.4 ± 2.4 | | 42.9 ± 5.1 | 9.7 | 24.7 ± 4.9 | 5.6 | 5.2 ± 0.8 | 1.2 |
| 110 | 2.1 ± 0.8 | | 16.0 ± 5.5 | 7.6 | 9.8 ± 1.4 | 4.7 | 2.9 ± 1.3 | 1.4 |
| 111 | 0.7 ± 0.2 | | 11.1 ± 1.0 | 16.6 | 3.9 ± 0.4 | 5.8 | 0.3 ± 0.1 | 0.5 |
| 112 | 3.2 ± 0.1 | | 31.9 ± 3.1 | 10.0 | 16.1 ± 4.1 | 5.1 | 3.2 ± 0.3 | 1.0 |
| 113 | 0.4 ± 0.1 | | 11.6 ± 6.7 | 31.7 | 3.9 ± 1.1 | 10.5 | 2.1 ± 1.9 | 5.8 |
| 114 | 3.3 ± 0.2 | | 27.7 ± 3.2 | 8.3 | 12.2 ± 7.4 | 3.7 | 6.6 ± 2.6 | 2.0 |
| 115 | 4.3 ± 0.4 | | 83.0 ± 2.0 | 19.2 | 65.3 ± 11.9 | 15.1 | 9.6 ± 1.3 | 2.2 |
| 116 | 8.6 ± 1.2 | | 32.3 ± 2.7 | 3.8 | 42.9 ± 10.3 | 5.0 | 9.6 ± 1.0 | 1.1 |

Figure 12

| Compound | Cell Line KB-31 IC$_{50}$ (nM) | KB-8511 IC$_{50}$ (nM) |
|---|---|---|
| Epo B | 0.19 | 0.12 |
| 3 | 0.11 | 0.07 |
| 104 | 0.20 | 0.12 |
| 106 | 0.44 | 0.29 |
| 108 | 3.04 | 2.67 |
| 109 | 10.0 | 6.73 |
| 110 | 1.16 | 1.28 |
| 111 | 0.72 | 0.55 |
| 113 | 0.54 | 0.41 |
| 114 | 4.87 | 3.24 |
| 115 | 8.38 | 7.37 |
| 116 | 9.01 | 11.65 |

| Compound | 1A9 IC$_{50}$ | A8 (β274) IC$_{50}$ | RR | PTX10 (β270) IC$_{50}$ | RR | PTX22 (β364) IC$_{50}$ | RR |
|---|---|---|---|---|---|---|---|
| epothilone A (Epo A) 1 | 3.1 ± 0.72 | 77.3 ± 9.25 | 24.9 | 29.1 ± 7.24 | 9.4 | 10.1 ± 2.10 | 3.3 |
| epothilone B (Epo B) 2 | 0.3 ± 0.05 | 6.5 ± 1.70 | 21.7 | 3.7 ± 1.83 | 12.3 | 2.1 ± 1.45 | 7 |
| paclitaxel (Taxol®) | 1.3 ± 0.22 | 11.3 ± 0.83 | 8.7 | 47.7 ± 5.01 | 36.7 | 29.4 ± 3.69 | 22.6 |
| tmt-epo B 3 | 0.17 ± 0.08 | 1.3 ± 0.65 | 7.6 | 0.26 ± 0.11 | 1.5 | 0.25 ± 0.17 | 1.5 |
| cis-CP-py-epo A 4 | 2.4 ± 0.99 | 41.6 ± 8.58 | 17.3 | 19.2 ± 9.39 | 8 | 4.2 ± 2.18 | 1.8 |
| trans-CP-epo A 5 | 10.1 ± 6.59 | 33.9 ± 5.56 | 3.4 | 17.2 ± 5.97 | 1.7 | 4.7 ± 1.68 | 0.5 |
| trans-CP-epo B 6 | 15 | >150 | >10 | 52 | 3.5 | 5 | 0.3 |
| trans-CP-py-epo A 7 | 0.6 ± 0.22 | 10.1 ± 2.07 | 16.8 | 5.9 ± 1.96 | 9.8 | 1.4 ± 0.51 | 2.3 |
| trans-CP-py-epo B 8 | 1.7 ± 0.76 | 27.9 ± 6.73 | 16.4 | 10.9 ± 3.52 | 6.4 | 5.6 ± 3.24 | 3.3 |
| trans-CP-pyOH-epo A 9 | 0.7 ± 0.16 | 13.0 ± 2.17 | 18.6 | 6.1 ± 1.90 | 8.7 | 1.1 ± 0.38 | 1.6 |
| trans-CP-pyOH-epo B 10 | 1.7 ± 1.12 | 13.2 ± 5.02 | 7.8 | 10.2 ± 3.75 | 6 | 2.5 ± 1.41 | 1.5 |
| trans-CP-tmt-epo A 11 | 1.2 ± 0.67 | 11.2 ± 2.30 | 9.3 | 3.2 ± 1.13 | 2.7 | 0.8 ± 0.38 | 0.7 |
| trans-CP-tmt-epo B 12 | 3.5 ± 1.64 | 28.9 ± 8.01 | 8.3 | 5.7 ± 1.96 | 1.6 | 11.5 ± 3.86 | 3.3 |
| trans-CP-5tmpy-epo B 13 | 14.2 ± 5.73 | 94 ± 5 | 6.6 | 72.0 ± 10.41 | 5.1 | 20.6 ± 9.06 | 1.5 |
| trans-CP-6tmpy-epo B 14 | 114 | >150 | >1.3 | >150 | >1.3 | 104 | 0.9 |

Figure 15

| Compound | % TP[a] | KB-31[b] | KB-8511[b] | RR |
|---|---|---|---|---|
| epothilone A (Epo A) 1 | 78 | 2.15[c] | 1.91[c] | 0.88[c] |
| epothilone B (Epo B) 2 | 93 | 0.19[c] | 0.18[c] | 0.95[c] |
| paclitaxel (Taxol®) | 52 | 2.92[c] | 626[c] | 214[c] |
| Tmt-epo B 3 | 99 | 0.11 | 0.07 | 0.61 |
| cis-CP-py-epo A 4 | 100[c] | 0.62[c] | 0.45[c] | 0.72[c] |
| trans-CP-epo A 5 | 100[c] | 0.97[c] | 0.64 | 0.66[c] |
| trans-CP-epo B 6 | 82 | 1.84 | 1.09 | 0.59 |
| trans-CP-py-epo A 7 | 94[c] | 0.84[c] | 0.68[c] | 0.81[c] |
| trans-CP-py-epo B 8 | 89 | 0.90 | 0.61 | 0.68 |
| trans-CP-pyOH-epo B 10 | 87 | 0.44 | 0.55 | 1.25 |
| trans-CP-tmt-epo A 11 | 93 | 0.66 | 0.32 | 0.48 |
| trans-CP-tmt-epo B 12 | 91 | 0.67 | 0.45 | 0.67 |
| trans-CP-5tmpy-epo B 13 | 88 | 6.88 | 5.28 | 0.77 |
| trans-CP-6tmpy-epo B 14 | 58 | 109 | 74 | 0.68 |

Figure 16

| Compound | Kd (37 °C)[b] | ΔG°app (37 °C)[c] |
|---|---|---|
| epothilone A (Epo A) 1 | 34 ± 4 | -44.5 ± 0.3 |
| epothilone B (Epo B) 2 | 1.6 ± 0.1 | -52.6 ± 0.5 |
| paclitaxel (Taxol®) | 93 ± 26 | -42.2 ± 0.2 |
| tmt-epo B 3 | 0.64 ± 0.24 | -54.5 ± 1.2 |
| cis-CP-py-epo A 4 | 5.2 ± 0.8 | -49.4 ± 0.3 |
| trans-CP-epo A 5 | 6.5 ± 0.1 | -48.6 ± 0.1 |
| trans-CP-epo B 6 | 8.0 ± 1.8 | -48.0 ± 0.1 |
| trans-CP-py-epo A 7 | 2.1 ± 0.4 | -51.5 ± 0.2 |
| trans-CP-py-epo B 8 | 1.9 ± 0.6 | -51.8 ± 0.8 |
| trans-CP-pyOH-epo B 10 | 6.0 ± 0.6 | -48.9 ± 0.3 |
| trans-CP-tmt-epo A 11 | 1.6 ± 0.5 | -52.2 ± 0.9 |
| trans-CP-tmt-epo B 12 | 1.8 ± 0.2 | -51.8 ± 0.3 |
| trans-CP-5tmpy-epo B 13 | 1.9 ± 0.3 | -51.6 ± 0.5 |
| trans-CP-6tmpy-epo B 14 | 53 ± 8 | -43.1 ± 0.5 |

ANALOGS OF EPOTHILONE

CROSS-REFERENCE TO RELATED APPLICATION

This is a nonprovisional application claiming priority from and is a continuation-in-part application of provisional U.S. patent application Ser. No. 60/400,535, filed Aug. 2, 2002 and of provisional U.S. patent application, filed Jun. 24, 2003, Ser. No. 60/480,933 (Express Mail Number EV331243442US).

This invention was made with United States Government support under Grant Nos. 5-P01 CA78045 and CA88822 by the National Institutes of Health. The United States Government has certain rights in the invention.

TECHNICAL FIELD

The invention relates to antitumor agents. More particularly, the invention related to analogs of epothilone as antitumor agents.

BACKGROUND

The epothilones e.g. 1(A) and 2(B), FIG. 1B, are a class of molecules having potent cytotoxicity against tumor cells, including Taxol™ (paclitaxel) resistant cell lines. Within this class, it has been observed that cyclopropane- and pyridine-containing analogs of epothilones B and compound 106 exhibit outstanding biological profiles as potential antitumor agents. Herein are disclosed designed analogs of epothilone B characterized by such structural motifs, but having enhanced cytotoxicity against tumor cells and/or enhanced biological profiles as potential antitumor agents.

SUMMARY

Disclosed herein are a number of rationally designed epoxide and cyclopropane epothilone B analogs with substituted side-chains. These analogs have been evaluated with respect to their biological activities against a series of human cancer cell lines. Among the several bioactive analogs, the novel cyclopropyl epothilone B analog 104 with a thiomethyl thiazole ring stands out as the most potent. This compound is 6-fold more active than the naturally occurring epothilone B (2) and appears to be, together with its oxygen counterpart 3, the most potent epothilone B analog synthesized to date. Previous structure-activity relationship studies (Nicolaou, K. C.; et al. Chem. Commun. 2001, 1523–1535; Nicolaou, K. C.; et al. ChemBioChem. 2001, 2, 69–75; Nicolaou, K. C.; et al. Tetrahedron 2002, 58, 6413–6432.) together with the data presented herein reconfirm that the epoxide oxygen is not required for biological activity within this class of small molecules and that the lipophilic thiomethyl group on the thiazole moiety enhances considerably the potency of these compounds. Lacking the relatively reactive epoxide moieties of 2 and 3, epothilone 104 may be endowed with certain advantages over the former compounds with regards to stability and side effects and, therefore, it may present a unique opportunity for clinical development.

The invention is directed to analogs of epothilone having potent cytotoxic active against a variety of cell lines, including Taxol®-resistant tumor cells. Another aspect of the invention is directed to the use of such compounds as cytotoxic agents.

One aspect of the invention is directed to a compound represented by formula I:

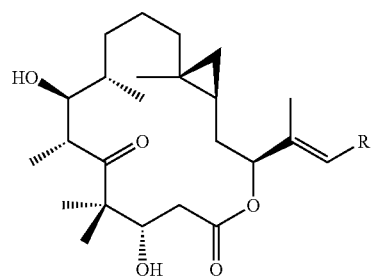

In Formula I, R is a radical selected from the group consisting of the following structures:

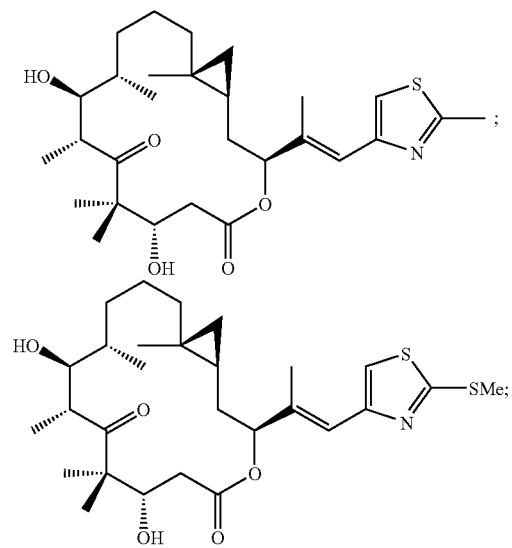

Preferred embodiments of this aspect of the invention include compounds represented by the following formulae:

-continued

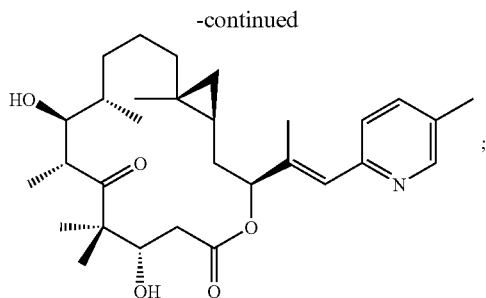

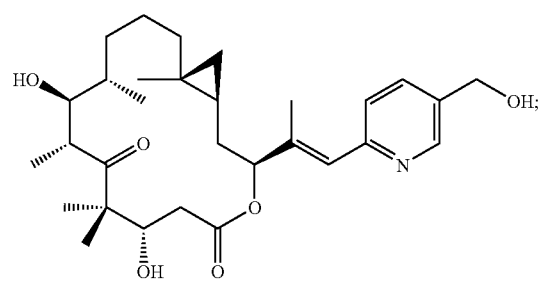

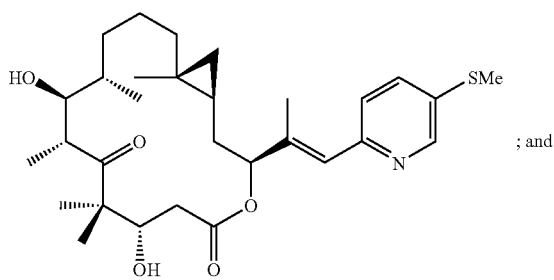
; and

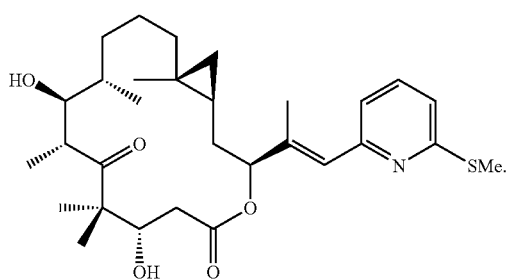

Another aspect of the invention is directed to a compound represented by formula II:

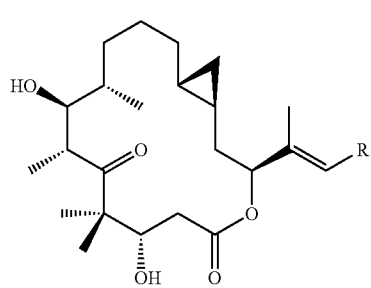

II

In formula II, R is a radical selected from the group consisting of the following structures:

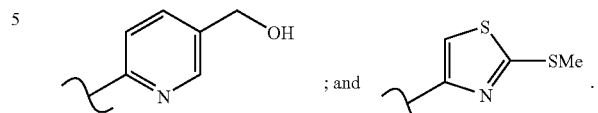
; and

Preferred embodiments of this aspect of the invention are represented by the following formula:

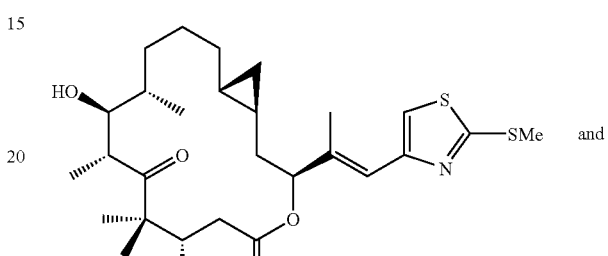
and

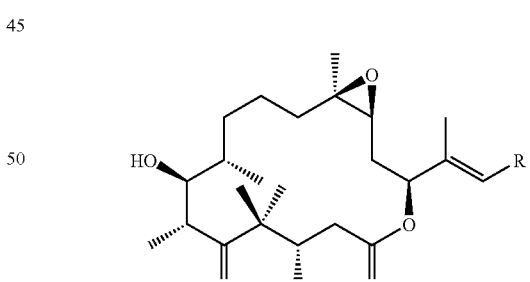

Another aspect of the invention is directed to a pharmaceutical composition containing a therapeutic dose of a compound within either formula I or formula II, represented above, for the treatment of a proliferative disease in a mammal. In a preferred mode, the mammal is a human.

Another aspect of the invention is directed to a compound represented by the following structure:

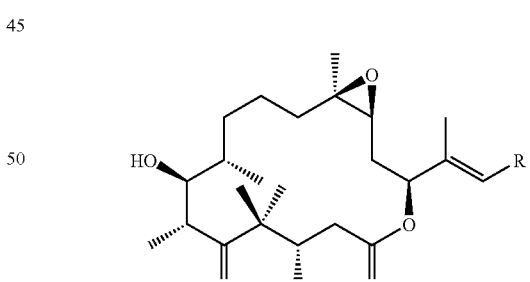

In the above structure, R is a radical selected from the group consisting of radicals represented by the following structures:

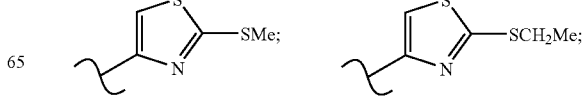

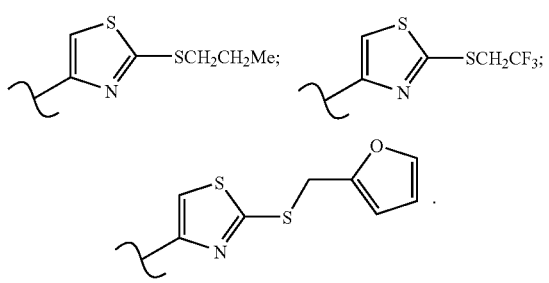

Preferred embodiments of this aspect of the invention include compound represented by the following structures:

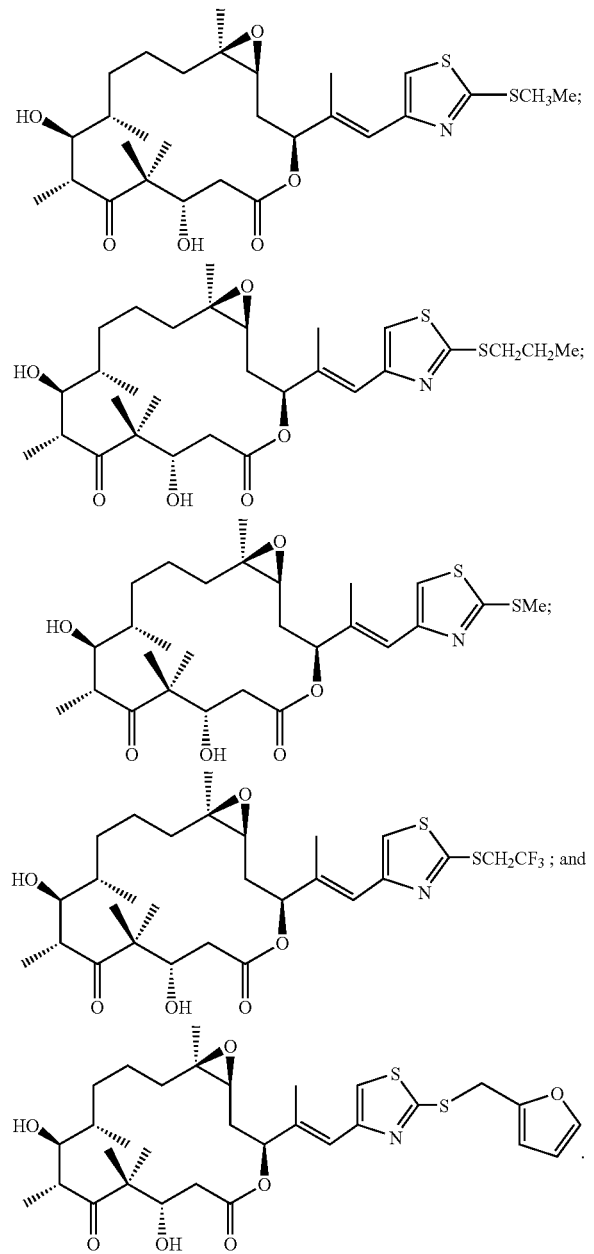

Another aspect of the invention is directed to a compound represented by the following structure:

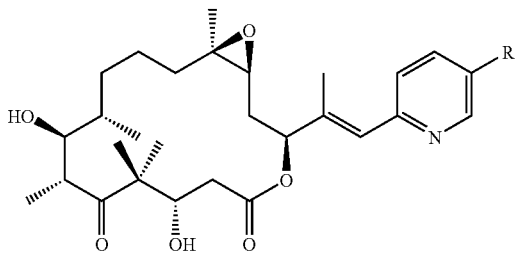

In the above structure, R is a radical selected from group consisting of —Me, —Cl, —Br, —SMe, and —CF$_3$. Preferred embodiments of this aspect of the invention include compounds represented by the following structures:

Other aspects of the invention are directed to compounds represented by the following structures:

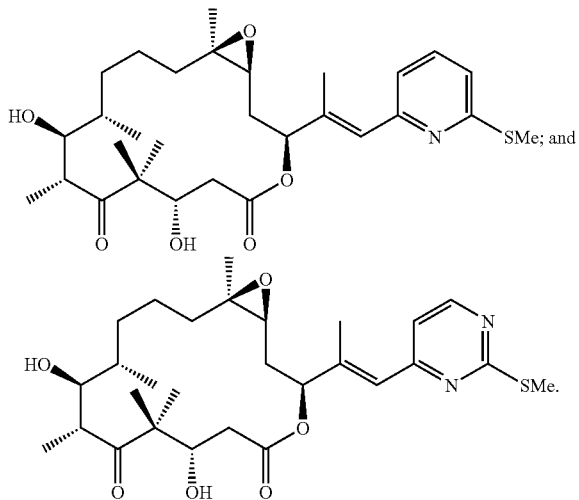

Another aspect of the invention is directed to a compound represented by the following structure:

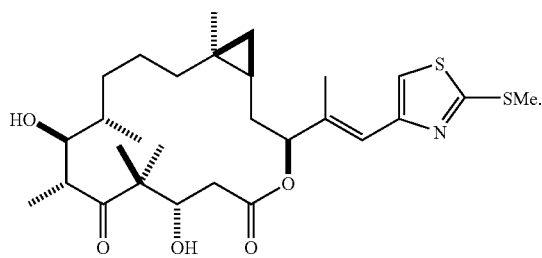

Another aspect of the invention is directed to a compound represented by the following structure:

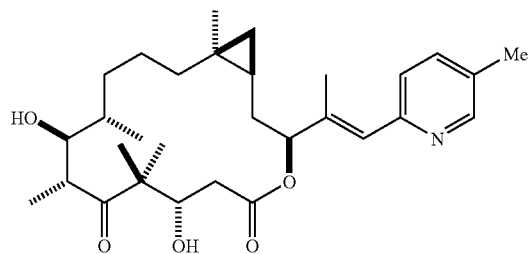

BRIEF DESCRIPTION OF DRAWINGS

FIG. 12 illustrates a table with the cytotoxicities of epothilones 104, 106 and 107–116 against human carcinoma cells and β-tubulin mutant cell lines selected with paclitaxel or epothilone A.

FIG. 13 illustrates a table with the cytotoxicities ($IC_{50}$'s in nM) of selected epothilones against the human epidermoid cell lines KB-3 and KB-8511.

FIG. 14 illustrates a table disclosing the cytotoxicity of epothilones 1 through 14 and paclitaxel against 1A9 human ovarian carcinoma cells and β-tubulin mutant cell lines selected with paclitaxel or epothilone A.

FIG. 15 illustrates a table disclosing the tubulin polymerization potency and cytotoxicity of epothilones 1–8, 10–14, and paclitaxel against human epidermoid cancer cell lines.

FIG. 16 illustrates a table disclosing binding affinities of epothilone analogues to the taxoid binding site of microtubules.

DETAILED DESCRIPTION

The construction of a series of epoxide and cyclopropane epothilones with varying side chains by chemical synthesis and biologically evaluated is disclosed. The biological evaluation of these compounds led to the identification of the thiomethylthiazole side chain as a desirable pharmacophoric group improving the biological activity of the epothilones with regard to cytotoxicity and tubulin polymerizing properties. The enhanced activity was confirmed by three distinct biological assays where the effects of the compounds tested were determined both in cells and in vitro.

Figure 3:
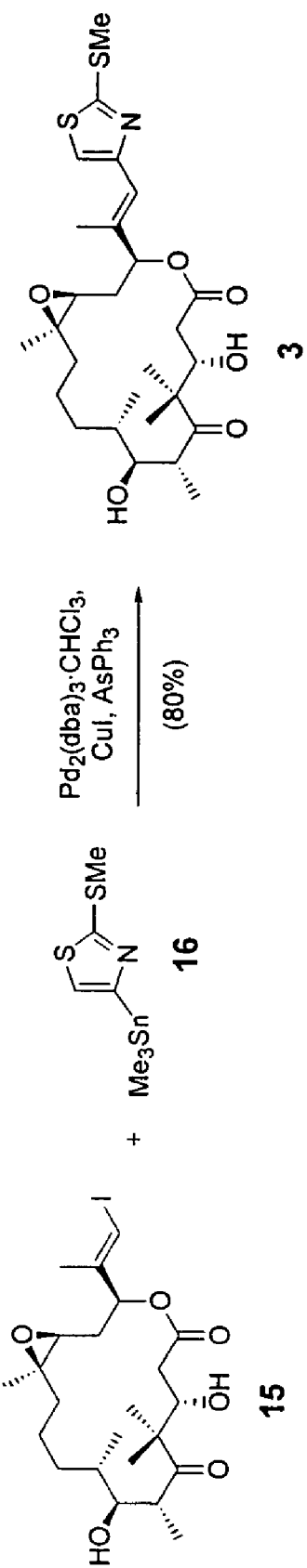
FIG. 3 illustrates the synthesis of 2-(thiomethyl)thiazole epothilone B (3) via Stille coupling.

Design and Chemical Synthesis of Epothilone Analogues:

As an initial foray, we decided to confirm the potency enhancement bestowed on the epothilone scaffold by the methylthio group as compared to the methyl substituent in the epothilone B series. The methylthiothiazole epothilone B (3) was thus synthesized by Stille coupling of stannane 16 (Nicolaou, K. C.; et al. Bioorg. Med. Chem. 1999, 7, 665–697) with vinyl iodide 15 (Nicolaou, K. C.; et al. Chem. Eur. J. 2000, 6, 2783–2800) (80% yield) as shown in FIG. 3. The observed high potency of analogue 3 against a series of tumor cell lines (see Table 1) encouraged us to proceed with the design and synthesis of an entire family of methylthio analogues as well as a number of new pyridine-containing epothilones.

Figure 4:
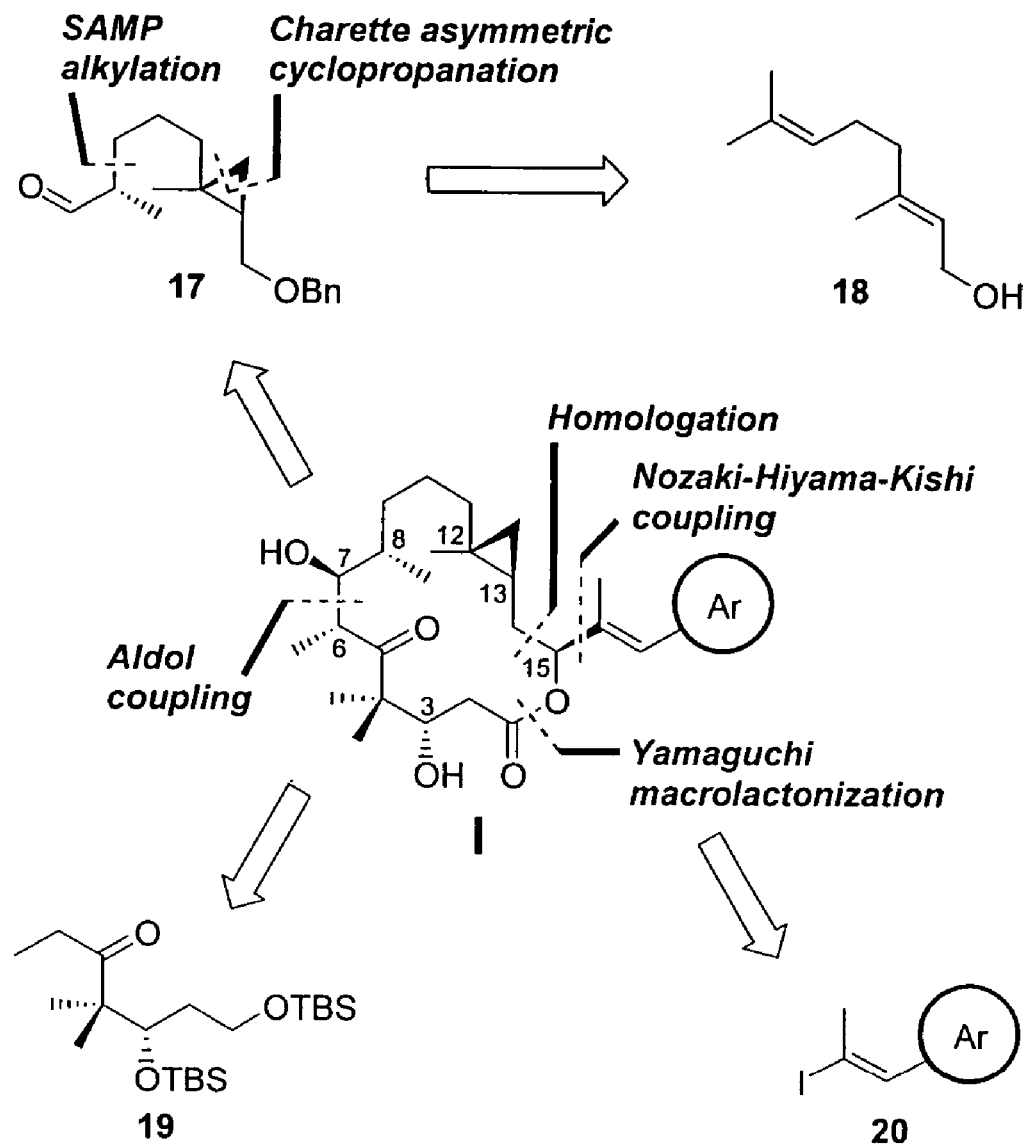
FIG. 4 illustrates a retrosynthetic analysis of trans-cyclopropyl epothilone B analogues (1–6, 8, 10, and 12–14).

FIG. 4 outlines, in retrosynthetic format, the pathway that was followed for the construction of the designed epothilone B analogues. Based on our previously reported strategy, the adopted sequence required a Charette cyclopropanation reaction (Nicolaou, K. C.; et al. J. Am. Chem. Soc. 2001, 123, 9313–9323; Charette, A. B.; et al. *J. Am. Chem. Soc.* 1998, 120, 11943–11952) to establish early on in the synthesis the 12,13-cyclopropyl site, an aldol reaction according to our optimized procedure (Nicolaou, K. C.; et al. *Chem. Eur. J.* 2000, 6, 2783–2800) to construct the C6–C7 bond with its two stereocenters, a Nozaki-Hiyama-Kishi coupling (Nicolaou, K. C.; et al. *J. Am. Chem. Soc.* 2001, 123, 9313–9323; Takai, K.; et al. *Tetrahedron Lett.* 1983, 24, 5281–5284; Jin, H.; et al. *J. Am. Chem. Soc.* 1986, 108, 5644–5646) to introduce the side chain, and a Yamaguchi macrolactonizaion (Inanaga, J.; et al. *Bull. Chem. Soc. Jpn.* 1979, 52, 1989–1993; Mulzer, J.; et al. *Synthesis* 1992, 215–228; Nicolaou, K. C.; et al. *J. Am. Chem. Soc.* 1997, 119, 7974–7991) to complete the macrocyclic structure. Key building blocks 18, 19, and 20 were thus defined as the starting points for these constructions. Construction of the corresponding epothilone A analogues was envisaged to be carried out in the same manner as previously reported by us (Nicolaou, K. C.; et al. *J. Am. Chem. Soc.* 2001, 123, 9313–9323).

Scheme 3 outlines the synthesis of the required aldehyde 32 from the readily available geraniol (18). Thus, Charette cyclopropanation of 18 ($Et_2Zn$—$CH_2I_2$, in the presence of chiral ligand 21) (Charette, A. B.; et al. *J. Am. Chem. Soc.* 1998, 120, 11943–11952) furnished cyclopropyl alcohol 22 in 87% yield and 93% ee. Protection of the hydroxy group in 22 (NaH-BnBr) (for abbreviations of reagents and protecting groups, see legends in schemes) followed by ozonolysis ($O_3$; $NaBH_4$) of the remaining double bond led to compound 23 in 89% overall yield. Conversion of alcohol 23 to the corresponding iodide (24, 95% yield) was accomplished upon mesylation and subsequent reaction with NaI. Alkylation of (−)-propionaldehyde SAMP hydrazone (25) (Nicolaou, K. C.; et al. *J. Am. Chem. Soc.* 1997, 119, 7974–7991; Enders, D. *Aymmetric Synth.* 1984, 3, 275–339; Enders, D.; Klatt, M. *Synthesis* 1996, 1403–1418) with iodide 24 under the influence of LDA gave compound 26 (84% yield), whose cleavage (MeI; $HCl_{aq}$) led to aldehyde 17 in 86% yield. The ratio of the resulting C-8 epimers was determined to be ca. 97:3 by $^1H$ NMR analysis of the MTPA esters derived from aldehyde 17 (Tsuda, M.; Endo, T.; Kobayashi, J. *J. Org. Chem.* 2000, 65, 1349–1352 and references cited therein). The aldol condensation between ketone 19 and aldehyde 17 under the previously defined conditions [LDA (2.4 equiv), ketone 19 (2.3 equiv), −78 to −40° C., 30 min; then aldehyde 17, −78° C., 5 min] (Nicolaou, K. C.; et al. *Chem. Eur. J.* 2000, 6, 2783–2800) afforded aldol product 27 which was isolated in a diastereomerically pure form (81% yield). Subsequent protection of the secondary alcohol in 27 as a TBS ether (TBSOTf, 2,6-lutidine) followed by selective cleavage of the primary TBS group (HF.py) afforded, in 88% overall yield, alcohol 28. The latter compound was stepwise oxidized to the carboxylic acid (DMP; then $NaClO_2$) which was then protected as the TMSE ester 29 (TMSE-OH, EDC, 4-DMAP) in 75% overall yield. Hydrogenolysis of the benzyl ether in 29 followed by oxidation with DMP led to aldehyde 30 (84% yield) whose homologation (NaHMDS—$MeOCH_2PPh_3Cl$; then PPTS) to the coveted higher aldehyde 32 proceeded smoothly, and via vinyl ether 31 (ca. 1:1 E:Z ratio), with 82% overall yield.

The side chains (20a–g, Scheme 4) were synthesized either as previously reported (20a and 20b) (Nicolaou, K. C.; et al. *J. Am. Chem. Soc.* 2001, 123, 9313–9323) or from the corresponding aryl halides (33 (Ellingboe, J. W.; et al. *J. Med. Chem.* 1994, 37, 542–550), 37, 38, 39) as shown in Scheme 4. Protection of 4-hydroxymethyl-2-pyridyl bromide 33 as a trityl ether (TrCl, 4-DMAP, 100%) followed by Sonogashira coupling (Arcadi, A.; et al. *Tetrahedron* 1994, 50, 437–452) of the resulting aryl bromide 34 with propyne [$Pd(PPh_3)_2Cl_2$—CuI, 96%] led to acetylenic compound 35 which served as a precursor to vinyl iodide 20c (n-BuLi; then $(n-Bu_3Sn)_2$, CuCN, MeOH; then $I_2$, 80% yield). Exchange of the trityl for a MOM group within 35 [HCl(g), $CHCl_3$; then NaH, MOM-Cl, 34% overall yield] (Betzer, J.-F.; et al. *Tetrahedron Lett.* 1997, 38, 2279–2282) allowed access to vinyl iodide 20d (67% yield) by exposure of the resulting intermediate 36 to the same conditions described above for the 35 to 20c conversion. Similar chemistry was employed to construct vinyl iodides 20e–20g from 37–39, respectively, as shown in Scheme 4.

Two crucial bond formations and two accompanying deprotections separated key building blocks 32 (prepared in this study for epothilone B analogues), 40 (prepared as previously described for epothilone A analogues) (Nicolaou, K. C.; et al. *J. Am. Chem. Soc.* 2001, 123, 9313–9323), and 20a–g (for side chains) from the targeted epothilone analogues. The first operation was the Nozaki-Hiyama-Kishi coupling (Takai, K.; et al. *Tetrahedron Lett.* 1983, 24, 5281–5284; Jin, H.; et al. *J. Am. Chem. Soc.* 1986, 108, 5644–5646) of aldehydes 32 and 40 with vinyl iodides 20a–g. This carbon-carbon bond forming reaction worked admirably in this instance ($CrCl_2$, $NiCl_2$, 4-t-BuPy, DMSO), furnishing, after TBAF-induced carboxylic acid generation, coupling products (41a, 41b, 41d–g, 42c and 42e) in yields indicated in Scheme 5 (as ca. 1:1 mixtures of C-15 diastereomers). Each mixture of hydroxy acid diastereomers (41a, 41b, 41d–g, 42c and 42e) was then subjected to Yamaguchi macrocyclization (2,4,6-trichlorobenzoyl chloride, 4-DMAP) to afford the desired 15(S) lactone in the indicated (unoptimized) yields together with its 15(R) epimer. The separation of the two epimers at this juncture was facilitated by their rather drastically different $R_f$ values on silica gel. Final deprotection of protected derivatives either with 20% TFA in $CH_2Cl_2$ (43a, 43b, 43e–g, 44c and 44e) or with TMSBr-4 Å MS in $CH_2Cl_2$, followed by 20% TFA in $CH_2Cl_2$ (43d), led to epothilones 6, 8–14 in the indicated (unoptimized) yields (Scheme 5). Chromatographically and spectroscopically pure compounds were subjected to biological evaluations as described below.

Chemical Biology:

The biological activities of the synthesized epothilones were evaluated through cytotoxicity, in vitro tubulin polymerization, and tubulin binding assays. Cytotoxicity was first evaluated in a set of ovarian carcinoma cell lines, including a parental cell line (1A9) and three drug-resistant cell lines, namely the paclitaxel-resistant strains (Giannakakou, P.; et al. *J. Biol. Chem.* 1997, 272, 17118–17125) 1A9/PTX10 and 1A9/PTX22 and the epothilone-resistant strain (Giannakakou, P.; et al. *Proc. Natl. Acad. Sci. U.S.A.* 2000, 97, 2904–2909) 1A9/A8. These resistant cell lines harbor distinct acquired β-tubulin mutations which affect drug-tubulin interaction and result in impaired taxane and epothilone-driven tubulin polymerization. The results of these biological investigations are summarized in Table 1 (Skehan, P.; et al. *J. Natl. Cancer Inst.* 1990, 82, 1107–1112). Further cytotoxicity and in vitro tubulin polymerization assays were carried out using a set of human epidermoid cancer cell lines, including a parent cell line (KB-31) and a paclitaxel-resistant (due to Pgp overexpression) cell line (KB-8511). The results of these studies are summarized in Table 2 (Nicolaou, K. C.; et al. *Chem. Biol.* 2000, 7, 593–599; Meyer, T.; et al. *Int. J. Cancer* 1989, 43, 851–856).

In general, there is good agreement between the in vitro tubulin polymerization potency and the cytotoxicity profile of the tested compounds against both the 1A9 human ovarian carcinoma cells and the KB-31 human epidermoid carcinoma cells. In agreement with original observations with the naturally occurring epothilones A and B, none of the epothilone A or B analogues tested herein appears to be a good substrate for the drug-efflux pump P-glycoprotein (Pgp). This is evident by the lack of cross-resistance of each of these analogues to the Pgp expressing cell line KB-8511, in contrast to paclitaxel-a known Pgp substrate—which is 214-fold less active against KB-8511 cells (see Table 2). It is noteworthy that all the epothilone analogues appear more active against the β-tubulin mutants compared to epothilone A (1) and epothilone B (2) (see Table 1, RR values). This is more pronounced with compounds 10–14 for which the relative resistance values (RR) range from 1.6–7.8 against PTX10 (β270) and A8 (β274) cells compared with 9.4–24.9 RR values for Epo A (1) and Epo B (2). Furthermore, in the current study, and in agreement with previous reports (Nicolaou, K. C.; et al. *ChemBioChem* 2001, 2, 69–75; Giannakakou, P.; et al. *J. Biol. Chem.* 1997, 272, 17118–17125; Giannakakou, P.; et al. *Proc. Natl. Acad. Sci. U.S.A.* 2000, 97, 2904–2909), we found that the paclitaxel-selected mutant PTX22 (β364) retains almost full sensitivity to the epothilones, and to all epothilone analogues tested in this report (RR values≦3.3).

Figure 2:
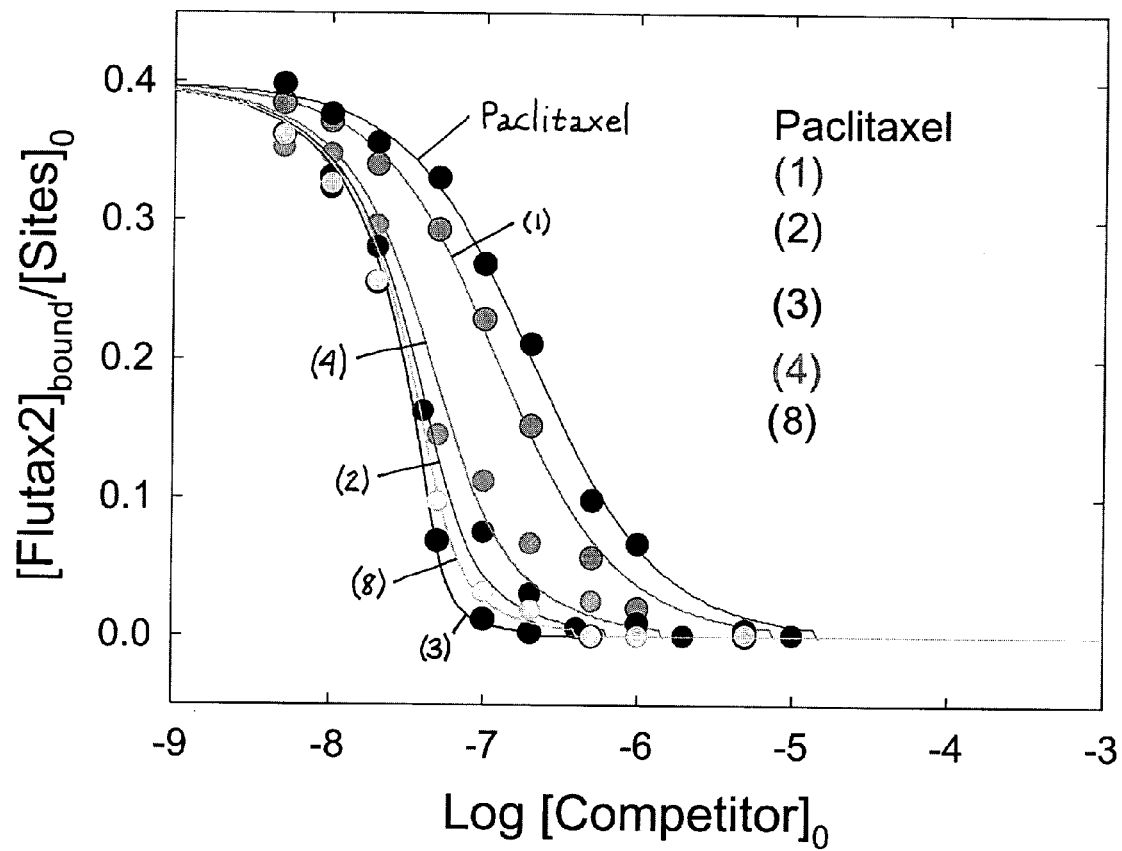
FIG. 2 illustrates a chart disclosing the displacement of the fluorescent taxoid Flutax-2 (50 nM) from microtubule binding sites (50 nM) by competing ligands at 37° C.

In addition to the above biological assays, the relative potency of each epothilone analogue was measured by the fluorescent taxoid displacement assay (Andreu, J. M.; Barasoain, I. *Biochemistry* 2001, 40, 11975–11984). The purpose of these experiments was to compare the equilibrium constants with which microtubules bind at their taxane site the epothilone analogues investigated. The inhibition of the binding of the well-characterized fluorescent taxoid Flutax-2 (Souto, A. A.; et al. *Angew. Chem. Int. Ed. Engl.* 1995, 34, 2710–2712; Diaz, J. F.; et al. *J. Biol. Chem.* 2000, 275, 26265–26276; Abal, M.; et al. *Cell. Motil. Cytoskeleton* 2001, 49, 1–15) to microtubules by each of the epothilone analogues was measured at 37° C. (FIG. 2). The resulting equilibrium dissociation constants shown in Table 3 indicate that epothilone A (1) has the lowest binding affinity among the epothilone analogues tested (Kd=34±4). The most powerful ligand among those measured in this assay is compound 3, with a Kd value of 0.64±0.24 nM, followed by compounds 8, 11–13, with similar Kd values comprised between 1.6 and 1.9 nM. With the possible exception of compound 13, the binding affinities of the analogues tested mirror their respective activities in both cell growth inhibition and in vitro tubulin polymerization assays.

Collectively from all three biological assays employed herein, a number of conclusions can be drawn in terms of structure-activity relationships within the epothilone family. First, the addition of the C12 methyl group does not enhance the activity in the trans-cyclopropyl series (compound 5 vs 6, 7 vs 8, 9 vs 10), contrary to the result in the cis epoxide series, where epothilone B (2) is at least 10-fold more active than epothilone A (1). This could be due to the different orientation of the C12 methyl group in the cis and trans compounds or to overall differences in conformation between the cis and trans compounds, although the details remain to be elucidated. Second, the introduction of the 2-thiomethylthiazole side chain enhances the activity compared with the natural 2-methylthiazole side chain (compounds 2 vs 3, 5 vs 11, and 6 vs 12). This effect was previously observed for epothilone C and D analogues (Nicolaou, K. C.; et al. *Angew. Chem.* 1997, 109, 2181–2187; *Angew. Chem. Int. Ed. Engl.* 1997, 36, 2097–2103; see also: Sinha, S. C.; et al. *ChemBioChem* 2001, 2, 656–665). Third, the replacement of a methyl group with a thiomethyl group in the pyridine side chain series (compounds 8 vs 13) reduces potency, contrary to the results obtained for the thiazole side chains above. This conclusion was based on the cell cytotoxicity and in vitro tubulin polymerization data, while in the fluorescent taxoid displacement assay the replacement of the methyl group with a thiomethyl moiety in the pyridine side chain is indifferent in terms of binding affinity. This discrepancy may simply reflect differences in cell uptake and permeability of the compounds tested or differences in the sensitivity of the two tubulin assays. Despite this discrepancy, it is clear from these data that the introduction of a thiomethyl group at the thiazole side chain is a more favorable modification than the introduction of a thiomethyl group at the pyridine side chain, which may be due to differing steric requirements by the two side chain scaffolds. In agreement with previous data obtained with cis pyridine epothilone analogues (Nicolaou, K. C.; et al. *Chem. Biol.* 2000, 7, 593–599), relocation of the thiomethyl group of the pyridine side chain from the position 5 (compound 13) to position 6 (compound 14) resulted in significant loss of activity. Fourth, mixed results are obtained with compounds 7 vs 9 and 8 vs 10 in which the 5-methylpyridine side chain (compounds 7 and 8) is substituted by the 5-hydroxymethylpyridine side chain (compounds 9 and 10). This substitution appears indifferent in cytotoxicity assays against the 1A9 human ovarian carcinoma cells (Table 1) where very similar $IC_{50}$ values are obtained for each pair (e.g. 0.6 and 0.7 nM for compounds 7 and 9, respectively; 1.7 nM for compounds 8 and 10). On the other hand, in the human epidermoid carcinoma cells KB-31, compound 10 is 2-fold more active than its counterpart compound 8 with $IC_{50}$s at 0.44 vs 0.9 nM, respectively. Given the small differences in the growth rate of the two human cancer cell lines that could account for the differential results, we could conclude that the introduction of the 5-hydroxymethylpyridine side chain is not likely to enhance activity in, at least, trans-12,13-cyclopropyl analogues of the epothilone family.

Design of Further Analogs:

The design of a further epothilone library was based on the current knowledge of structure activity relationships (SAR), specifically the facts that: (1) epothilone B (2) is considerably more potent than epothilone A (1); (2) a thiomethyl replacement for the methyl group on the thiazole moiety enhances the potency (Nicolaou, K. C.; et al. *Angew. Chem.* 1998, 110, 2120–2153; *Angew. Chem. Int. Ed.* 1998, 37, 2014–2045. Nicolaou, K. C.; et al. *Tetrahedron* 2002, 58, 6413–6432; Nicolaou, K. C.; et al. *Angew. Chem.* 1998, 110, 89–92; *Angew. Chem. Int. Ed.* 1998, 37, 84–87.); (3) a heterocycle such as pyridine (Nicolaou, K. C.; et al. *Chem. Biol.* 2000, 7, 593–599.) replacement for the thiazole ring needs to maintain the proper position for the nitrogen for biological activity; and (4) a cyclopropane ring can replace the epoxide moiety without loss of activity (Nicolaou, K. C.; et al. *J. Am. Chem. Soc.* 2001, 123, 9313–9323; Nicolaou, K. C.; et al. *ChemBioChem.* 2001, 2, 69–75; Johnson, J. A.; et al. *Org. Lett.* 2000, 2, 1537–1540.). From these considerations, epothilones 104, 106 and 107–116 (FIG. 1B) were considered as prime candidates for chemical synthesis and biological evaluation.

Figure 8:
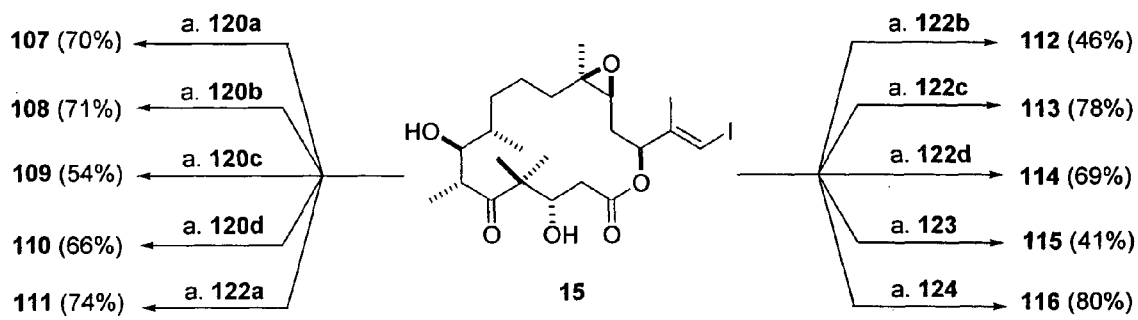
FIG. 8 is a scheme showing the last step in the synthesis of many of the analogs from the vinyl iodide 15.

The designed epothilone analogs (107–116) were synthesized in a convergent manner from vinyl iodide 15 (Nicolaou, K. C.; et al. *Chem. Eur. J.* 2000, 6, 2783–2800.) and the corresponding aromatic stannanes as shown in FIG. 8 (for abbreviations of reagents and protective groups, see the detailed description of figures). Thus, a Stille-type coupling of 15 with appropriate stannanes (120a–d, 122a–d, 123 and 124) was carried out in the presence of $PdCl_2(MeCN)_2$, CuI and $AsPh_3$ in DMF at ambient temperature, leading directly to the desired epothilones (107–116) in the indicated yields. The required aromatic stannanes were prepared as summarized in FIG. 9. Thus, for the thiazole compounds 120a–120d, the commercially available 2,4-dibromothiazole (118) was reacted with the corresponding thiol in the presence of NaH leading first to the intermediate sulfides (119a–119d) through replacement of the more reactive 2-bromide substituent. Subsequent coupling of these substrates with $Me_3SnSnMe_3$ in the presence of $Pd(PPh_3)_4$ in toluene at 100° C. then gave the desired products 120a–120d via reaction of the second bromide residue. The pyridyl stannanes 122a–122d were similarly synthesized from the readily available 2-bromopyridines 121a, 121b (Virgilio, N. *J. Org. Chem.* 1973, 38, 2660–2664), 38 (Nicolaou, K. C.; et al. *Tetrahedron* 2002, 58, 6413–6432) and 39 (Testaferri, L.; et al. *Tetrahedron* 1985, 41, 1373–1384) via metal-halogen exchange (nBuLi) followed by quenching of the resulting 2-lithioderivatives (Gilman, H.; et al. *J. Org. Chem.* 1951, 16, 1788–1791) with $nBu_3SnCl$. Stannanes 123 (Dinnell, K.; et al. *Bioorg. Med. Chem. Lett.* 2001, 11, 1237–1240) and 124 (Jessie, S.; Kjell, U. *Tetrahedron* 1994, 50, 275–284) were prepared according to the corresponding literature procedures from the respective halides.

Figure 10:
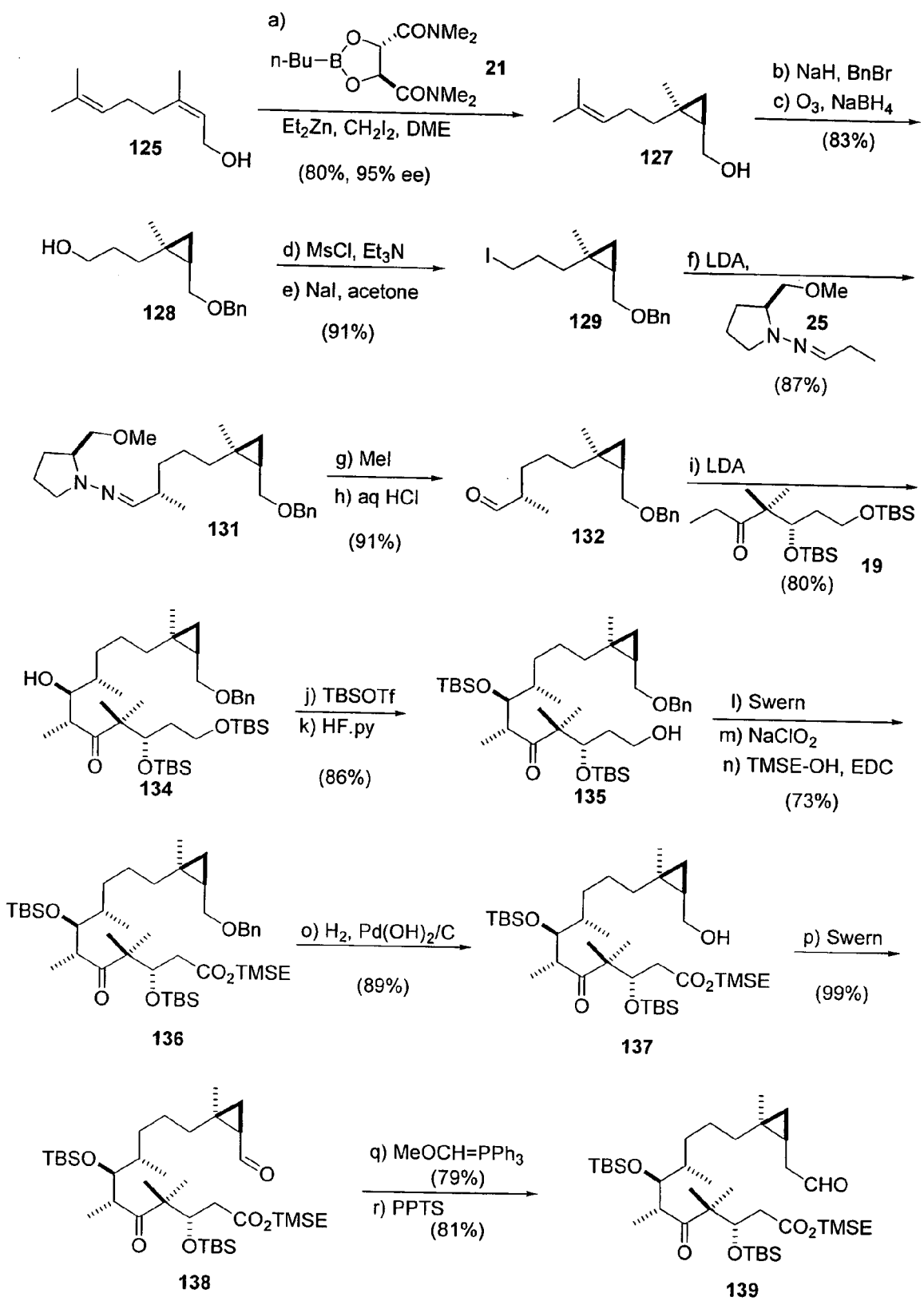
FIG. 10 illustrates a scheme showing the synthetic route taken to build the skeleton of the cyclopropyl analogs of epothilone B.

The chemical synthesis of cyclopropane epothilones 104 and 106 required the key aldehyde 139 which was constructed from nerol (125) as shown in FIG. 10. Thus, Charrette asymmetric cyclopropanation (Nicolaou, K. C.; et al. *J. Am. Chem. Soc.* 2001, 123, 9313–9323; Nicolaou, K. C.; et al. *Tetrahedron* 2002, 58, 6413–6432; Charette, A. B.; et al. *J. Am. Chem. Soc.* 1998, 120, 11943–11952.) of 125 in the presence of ligand 21 according to the literature, furnished cyclopropane alcohol 127 in 80% yield and 95% ee. The hydroxyl group in 127 was protected as benzyl ether (NaH, BnBr, 100%) and the resulting product was subjected to ozonolysis ($O_3$, $NaBH_4$) leading to primary alcohol 128 (83% yield). This alcohol was converted to the corresponding iodide (129) via mesylation (MsCl, $Et_3N$) and subsequent displacement of the intermediate mesylate with NaI (91% overall). Ender's alkylation (Enders, D. *Asymm. Synth.* 1984, 3, 275–339; Enders, D.; Klatt, M. *Synthesis* 1996, 1403–1418.) of (–)-SAMP hydrazone 25 with iodide 129 under the influence of LDA proceeded smoothly to afford hydrazone 131 (87% yield), whose cleavage (MeI; HCl aq) led to aldehyde 132 (91% yield). The crucial aldol reaction between ketone 19 (Nicolaou, K. C.; et al. *J. Am. Chem. Soc.* 1997, 119, 7974–7991.) (LDA) and aldehyde 132 proceeded smoothly and stereoselectively in THF:ether (1:1) at –78° C. to afford the desired hydroxy ketone 134 in 80% yield. Protection of the secondary alcohol in 134 as a silyl ether (TBSOTf, 2,6-lutidine) followed by selective removal of the primary TBS group (HF.py) furnished primary alcohol 135 (86% overall yield). The later compound (135) was then oxidized stepwise [$(COCl)_2$, DMSO, –78° C.; $NaClO_2$)] and the resulting carboxylic acid was protected as a TMSE ester (TMSE-OH, EDC, DMAP, 73% overall yield) to afford 136. Hydrogenolysis of the benzyl group within 136 [$H_2$, 10% $Pd(OH)_2$/C, 89% yield] led to alcohol 137, whose Swern oxidation [$(COCl)_2$, DMSO, $Et_3N$] led to the corresponding aldehyde 138 (99% yield). Homologation of this aldehyde (138) via Wittig olefination ($MeOCH_2P^+Ph_3Cl^-$, nBuLi, 79% yield) followed by acid hydrolysis (PPTS, 81% yield) of the resulting enol ether led to the targeted aldehyde 139.

Figure 11:
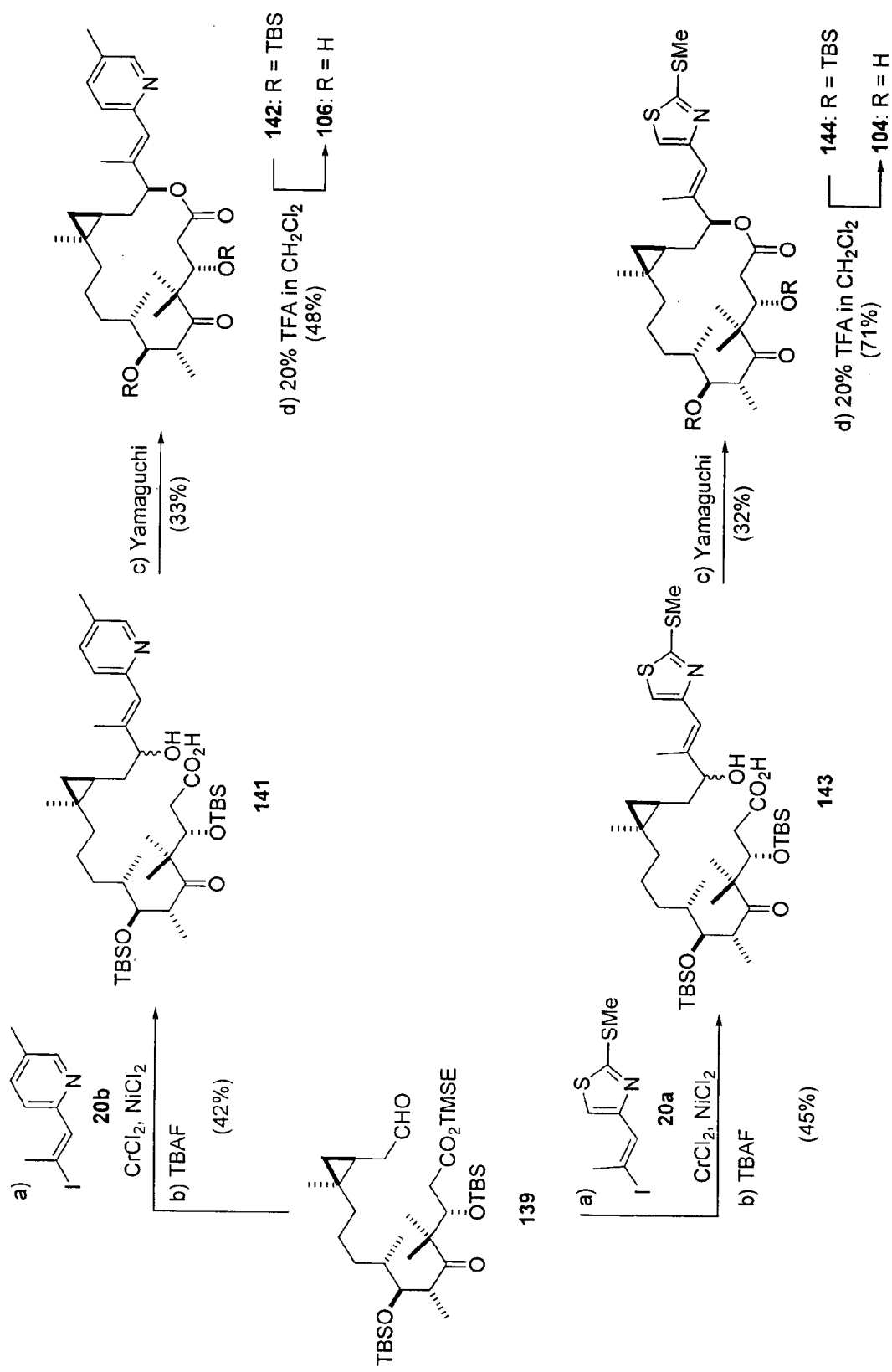
FIG. 11 illustrates a scheme showing the final steps used in the synthesis of cyclopropyl analogs 104 and 106.

Following a previously developed strategy towards epothilone analogs (Nicolaou, K. C.; et al. *J. Am. Chem. Soc.* 2001, 123, 9313–9323), aldehyde 139 (FIG. 11) was subjected to a Nozaki-Hiyama-Kishi coupling (Takai, K.; et al. *Tetrahedron Lett.* 1983, 24, 5281–5284; Jin, H.; et al. *J. Am. Chem. Soc.* 1986, 108, 5644–5646.) reaction with vinyl iodides 20a (Nicolaou, K. C.; et al. *J. Am. Chem. Soc.* 2001, 123, 9313–9323) and 20b (Nicolaou, K. C.; et al. *Tetrahedron* 2002, 58, 6413–6432) followed by TBAF treatment to afford the corresponding secondary alcohols 141 and 143 as mixtures (ca 1:1) of the two epimers (at C-15) (42–45% combined yield, unoptimized). These mixtures were then cyclized under Yamaguchi conditions, viz. 2,4,6-trichlorobenzoyl chloride, $Et_3N$, DMAP, toluene, 0–75° C. (Inanaga, J.; et al. *Bull. Chem. Soc. Jpn.* 1979, 52, 1989–1993; Mulzer, J.; et al. *Synthesis* 1992, 215–228) to afford the desired (15S) 16-membered lactones 142 (33% yield) and 144 (32% yield) together with their (15R)-epimers (ca 1:1 ratio, chromatographically separated, silica gel. Based on previous experience, (Nicolaou, K. C.; et al. *Tetrahedron* 2002, 58, 6413–6432) it was assumed that the desired (15S) macrolactones (142 and 144) eluted after their less polar (15R)-epimers, an assumption verified by their biological activities. Finally the TBS groups were removed from 142 and 144 by the action of TFA, leading to epothilones 106 (48% yield) and 104 (71% yield) (unoptimized yields) as shown in FIG. 11.

The biological activities of the synthesized epothilones were evaluated through cell growth inhibition assays (cytotoxicity assays). Cytotoxicity was first evaluated in a set of ovarian carcinoma cell lines, including a parental cell line (IA9) and three drug-resistant cell lines, namely the paclitaxel-resistant cell lines IA9/PTX10 and IA9/PTX22 (Giannakakou, P.; et al. *J. Biol. Chem.* 1997, 272, 17118–17125.) and the epothilone-resistant cell line 1A9/A8 (Giannakakou, P.; et al. *Proc. Natl. Acad. Sci.* 2000, 97, 2904–2909.). These resistant cell lines harbor distinct acquired β-tubulin mutations which affect drug-tubulin interaction and result in impaired taxane and epothilone-driven tubulin polymerization. The results of these biological investigations are summarized in FIG. 12. Further cytotoxicity studies were carried out using a set of human epidermoid cancer cell lines, including a parent cell line (KB-31), and a paclitaxel-resistant (due to Pgp overexpression) cell line (KB-8511). The results of these studies are summarized in FIG. 13.

There is a general agreement in the relative potency of the substituted epothilone B analogs against the 1A9 human ovarian and the KB-31 human epidermoid cancer cells. Collectively, the results of these cytotoxicity assays revealed interesting information in terms of structure-activity relationships within the epothilone family. First, compounds 104 and 106 in which the $C_{12}$–$C_{13}$ epoxide moiety is replaced by a cyclopropane ring are the two most potent compounds among all the epothilone B analogs presented here. This result reaffirms that the $C_{12}$–$C_{13}$ epoxide moiety is not necessary for biological activity as previously noted (Nicolaou, K. C.; et al. *J. Am. Chem. Soc.* 2001, 123, 9313–9323; Nicolaou, K. C.; et al. *ChemBioChem.* 2001, 2, 69–75; Johnson, J. A.; et al. *Org. Lett.* 2000, 2, 1537–1540.). Compound 104 is 6-fold more active than the parent epothilone B (2) against the 1A9 human ovarian carcinoma cells (FIG. 12) further confirming that the replacement of the methyl group on the thiazole side-chain with a thiomethyl group leads to increased activity. This result is in agreement with previous data on a similar substitution in epothilone B without replacement of the $C_{12}$–$C_{13}$ epoxide (i.e. compound 3) (Nicolaou, K. C.; et al. *Tetrahedron* 2002, 58, 6413–6432). The latter compound (3) was about 2-fold more active than the parent epothilone B, while compound 104 is 6-fold more potent than epothilone B. This result makes compound 104, the most active epothilone B analog against the 1A9 cell line synthesized to date and suggests that replacement of the epoxide by a cyclopropane moiety together with the replacement of the methyl substituent on the thiazole moiety with a thiomethyl group act synergistically, leading to the observed enhancement of biological activity. Interestingly, substitution of the methyl group of the thiazole ring with larger moieties (compounds 107–10) (The $IC_{50}$ value for compound 107 was found to be 2.5 nM against the 1A9 cell line.) led to diminished biological activity as compared to epothilone B (FIGS. 12 and 13).

Among the epothilone B analogs with substituted pyridine side-chains at the 5-position of the pyridine ring (compounds 111–113 and 115), the thiomethyl analog (compound 113) is the most potent followed by the bromo-substituted derivative (compound 111) followed by the chloro-substituted system (compound 112). When the thiomethyl group is relocated from the 5-position of the pyridine ring (compound 113) to the 6-position (compound 114) loss of activity occurs as the $IC_{50}$ value drops from 0.4 nM (compound 113) to 3.3 nM (compound 114) (FIG. 12). Furthermore, replacement of the thiomethyl group at the 5-position of the pyridine ring (compound 113) with a trifluoromethyl group (compound 115) results in loss of activity by 10-fold. Finally, the least active of the synthesized epothilone B analogs is compound 116 where a pyrimidine side-chain with a thiomethyl substitution has replaced the thiazole side-chain of the parent compound.

Varying degrees of cross-resistance are obtained with the substituted epothilone B analogs against the paclitaxel- and epothilone-resistant human ovarian carcinoma sub-lines (FIG. 12) ranging from 3- to 41-fold. These results suggest that the location of the tubulin mutations in these lines affects differentially the binding of each of the analogs to tubulin. Moreover, and in agreement with the original observations with the naturally occurring epothilones A and B, none of the epothilone B analogs tested herein appears to be a good substrate for the drug-efflux pump P-glycoprotein (Pgp). This is evident by the lack of cross-resistance of each of these analogs to the Pgp-expressing cell line KB-8511 (FIG. 13). In contrast, it has been previously shown that paclitaxel, a known Pgp substrate, was 214-fold less active against KB-8511 cells as compared to its action against their parental counterpart, non-Pgp-expressing KB-31 cells (Nicolaou, K. C.; et al. *Tetrahedron* 2002, 58, 6413–6432).

Experimental

General

All reactions were carried out under an argon atmosphere with dry solvents under anhydrous conditions, unless otherwise noted. Anhydrous solvents were obtained by passing them through commercially available activated alumina columns. All reagents were purchased at highest commercial quality and used without further purification. Reactions were generally monitored by thin-layer chromatography carried out on 0.25 mm E. Merck silica gel plates (60F-254). E. Merck silica gel (60, particle size 0.040–0.063 mm) was used for flash column chromatography. Preparative thin-layer chromatography (PTLC) separations were carried out on 0.25, 0.50 or 1 mm E. Merck silica gel plates (60F-254). Melting points (mp) are uncorrected and were recorded on a Thomas-Hoover Unimelt capillary melting point apparatus. Optical rotations were recorded on a Perkin-Elmer 241 polarimeter. NMR spectra were recorded on Bruker DRX-600, DRX-500, AMX-400 or AC-250 instruments and calibrated using residual undeuterated solvents as an internal reference. All labeling of carbon atoms, e.g. C15, refers to epothilone A (1) numbering (see FIG. 1). IR spectra were recorded on a Perkin-Elmer 1600 series FT-IR spectrometer. High resolution mass spectra were recorded on a PerSeptive Biosystems Voyager™ IonSpec mass spectrometer (MALDI-FTMS) or on an API 100 Perkin-Elmer mass spectrometer (ESI).

Synthesis of Epothilone 3

Stille Coupling of Vinyl Iodide 15 with Stannane 16.

A solution of $Pd_2(dba)_3(CHCl_3$ (3.9 mg, 3.8 µmol), $AsPh_3$ (4.6 mg, 15 µmol), and CuI (7.2 mg, 38 µmol) in DMF (degassed, 0.5 mL) was added at 25° C. to a solution of iodide 15 (10 mg, 19 µmol)(Nicolaou, K. C., et al., *Chem. Eur. J.* 2000, 6, 2783–2800) and stannane 16 (11 mg, 38 µmol) (Nicolaou, K. C., et al., *Bioorg. Med. Chem.* 1999, 7, 665–697) in DMF (degassed, 0.5 mL), and the resulting solution was stirred for 2 hours. Water (10 mL) was added, and the mixture was extracted with EtOAc (3(10 mL). The combined organic phase was washed with water (30 mL), brine (30 mL), and dried ($Na_2SO_4$). After evaporation of the volatiles, the residue was purified by flash column chromatography (sillica, hexanes:EtOAc 2:1 (1:1) to yield epothilone 3 as a white solid (7.2 mg, 72%); TLC $R_f$=0.29 (silica, hexanes:EtOAc 1:1); $[\alpha]_D22$–53 (c 0.51, $CH_2Cl_2$); IR (film) $v_{max}$ 3472 (br), 2967, 2920, 1731, 1684, 1461, 1420, 1378, 1249, 1143, 1032, 973, 879, 732, 667 $cm^{-1}$; MALDI-FTMS m/z 562.2267 ($MNa^+$), calcd for $C_{27}H_{41}NO_6S_2Na$ 562.2267.

Construction of Aldehyde 32

Alcohol 23. To a solution of cyclopropyl alcohol 22 (4.08 g, 24 mmol) (Charette, A. B.; et al. *J. Am. Chem. Soc.* 1998, 120, 11943–11952) in DMF (40 mL) was added sodium hydride (1.45 g, 36 mmol, 60% in mineral oil) portionwise with stirring at 0° C. After stirring for 0.5 h at 25° C., the mixture was cooled to 0° C., benzyl bromide (4.3 mL, 36 mmol) was added over 2 min, and stirring was continued for 12 h at 25° C. The reaction was quenched with $NH_4Cl$ (sat., 50 mL), the mixture was extracted with EtOAc (3(50 mL) and the combined extract was washed with brine (2(100 mL), dried ($Na_2SO_4$) and evaporated. The residue was dissolved in $CH_2Cl_2$:MeOH 4:1 (60 mL), and the solution was ozonized (100 L/h, ca. 5 g $O_3$/h) at –78° C. for 21 min. (NOTE: Longer reaction times must be avoided to prevent oxidation of the benzyl ether to the corresponding benzoate.) Excess ozone was removed by flushing with $N_2$ for 1 min, and then $NaBH_4$ (2.75 g, 73 mmol) was added in small portions (CAUTION! Exothermic!) followed by methanol (20 mL). The mixture was warmed to 25° C. over 1 hour, and the reaction was quenched by the addition of $NH_4Cl$ (sat., 20 mL). The mixture was extracted with $CH_2Cl_2$ (2(50 mL), and the combined extract was washed with brine (100 mL), dried ($Na_2SO_4$) and evaporated. The residue was purified by flash chromatography (silica, hexanes:EtOAc 5:2) to yield 23 as a yellow oil (5.07 g, 89%). TLC $R_f$=0.20 (silica, hexanes:EtOAc 3:1); $[\alpha]_D22$–7.5 (c 1.76, $CHCl_3$); IR (film)

$v_{max}$ 3390 (br), 2933, 2859, 1452, 1070, 739, 698 cm$^{-1}$; MALDI-FTMS m/z 257.1519 (MNa$^+$), calcd for $C_{15}H_{22}O_2Na$ 257.1512.

Iodide 24. To a solution of cyclopropyl alcohol 23 (10.08 g, 43.0 mmol) in dry CH$_2$Cl$_2$ (100 mL) at 0° C. was added methanesulfonyl chloride (4.2 mL, 54 mmol) followed by triethylamine (9.0 mL, 65 mmol) dropwise. A white precipitate started to form immediately. The mixture was stirred at 25° C. for 1 hour, then NH$_4$Cl (sat., 50 mL) and water (50 mL) were added and the phases were separated. The aqueous phase was extracted with EtOAc (100 mL), and the combined organic phase was washed with brine, dried (Na$_2$SO$_4$) and evaporated. The residue was dissolved in dry acetone (200 mL), and sodium iodide (19.3 g, 129 mmol) was added. The initially almost clear solution was refluxed for 40 min, during which time a white precipitate formed. Water (100 mL) was added and the mixture was extracted with ether (500+250 mL). The combined extract was dried and evaporated, and the residue was purified by flash chromatography (silica, hexanes:EtOAc 5:1) to yield 24 as a colorless oil (14.16 g, 95%). TLC R$_f$=0.66 (silica, hexanes:EtOAc 5:1); $[\alpha]_D$22−16 (c 2.05, CHCl$_3$); IR (film) $v_{max}$ 2916, 2848, 1453, 1217, 1098, 1073, 735, 697 cm$^{-1}$; ESI-MS m/z 367 (MNa$^+$), calcd for $C_{15}H_{21}IONa$ 367.

Hydrazone 26. A solution of LDA was prepared by adding n-BuLi (13.1 mL, 21.0 mmol, 1.6 M in hexanes) to diisopropylamine (2.94 mL, 21.0 mmol) in THF (10 mL) at −78° C., then warming the solution to 0° C., and stirring for 10 min. To this LDA solution was added propionaldehyde SAMP hydrazone 25 (3.32 g, 19.5 mmol) (Nicolaou, K. C., et al., *J. Am. Chem. Soc.* 1997, 119, 7974–7991; Enders, D. *Aymmetric Synth.* 1984, 3, 275–339; and Enders, D., et al., *Synthesis* 1996, 1403–1418), and the mixture was stirred for 6 h at 0° C., during which time a white precipitate formed. The mixture was cooled to −98° C. (MeOH/N$_2$(I) bath) and a solution of iodide 24 (5.16 g, 15.0 mmol) in THF (20 mL) was added over 0.5 hour. The reaction mixture was then allowed to warm to −10° C. over 14 hours, and then the reaction was quenched with NH$_4$Cl (sat., 10 mL). The mixture was extracted with EtOAc (100 mL+2(50 mL), the combined extract was dried (Na$_2$SO$_4$) and evaporated, and the residue was purified by flash chromatography (silica, hexanes:EtOAc 6:1 (4:1)) to yield hydrazone 26 as a yellow oil (4.88 g, 84%). TLC R$_f$=0.38 (silica, hexanes:EtOAc 5:1); $[\alpha]_D$22−61 (c 1.45, CHCl$_3$); IR (film) $v_{max}$ 2926, 1454, 1097, 736, 697 cm$^{-1}$; MALDI-FTMS m/z 387.3008 (MH$^+$), calcd for $C_{24}H_{39}N_2O_2$ 387.3006.

Aldehyde 17. A solution of hydrazone 26 (3.82 g, 9.9 mmol) in iodomethane (10 mL) was heated at 60° C. (reflux condenser) for 3 hours, and was then cooled to 25° C. Excess iodomethane was evaporated and traces removed under oil pump vacuum. The residual yellow syrup was vigorously stirred with 3 N HCl (190 mL) and pentane (190 mL) for 3 h at 25° C., the phases were separated, and the aqueous phase was extracted with pentane (100 mL). The combined organic phase was dried (Na$_2$SO$_4$, NaHCO$_3$) and evaporated to yield aldehtde 17 as a yellow oil (2.38 g, 88%). $[\alpha]_D$22+2 (c 1.3, CHCl$_3$); IR (film) $v_{max}$ 2931, 2856, 1724, 1454, 1095, 1074, 736, 698 cm$^{-1}$; MALDI-FTMS m/z 297.1830 (MNa$^+$), calcd for $C_{18}H_{26}O_2Na$ 297.1825.

Due to the configurational lability at C8 (epothilone numbering), the aldehyde should be used immediately in the next step. The dr at C8 was estimated as follows: A sample of 17 was treated with excess NaBH$_4$ in methanol for 10 min. The reaction was quenched with NH$_4$Cl (sat.), the mixture was extracted with EtOAc, and the extract was dried (Na$_2$SO$_4$) and evaporated. The residue was treated with (R)-(−)-MTPACl (2–3 equiv.), excess triethylamine and 4-DMAP in CH$_2$Cl$_2$ for 3 hours. Purification by preparative TLC yielded a sample of the (S)-MTPA ester, which by $^1$H NMR analysis showed a dr=97:3, with the correct absolute stereochemistry at C8 as the major isomer (Tsuda, M., et al., *J. Org. Chem.* 2000, 65, 1349–1352). Analogous results were obtained by using (S)-(+)-MTPACl.

Aldol product 27. A solution of LDA was prepared by adding n-BuLi (7.5 mL, 12 mmol, 1.6 M in hexanes) to diisopropylamine (1.68 mL, 12 mmol) in THF (12 mL) at −78° C., then warming the solution briefly to 0° C., and finally cooling back to −78° C. A solution of ketone 19 (4.63 g, 11.5 mmol) (Nicolaou, K. C., et al., *J. Am. Chem. Soc.* 1997, 119, 7974–7991) in THF (12 mL) was added dropwise over 2 min, and the mixture was stirred for 1 h at −78° C. and then for 0.5 h at −40° C. It was again cooled to −78° C., and a solution of aldehtde 17 (1.37 g, 5.0 mmol) in THF (25 mL), pre-cooled to −78° C., was added via cannula over 1 min, taking care to ensure minimal warming during transfer. The mixture was stirred for 5 min, and the reaction was then quenched by rapid injection of a solution of AcOH (1.4 mL) in THF (4.2 mL). After 5 min at −78° C., the mixture was warmed to 25° C. and partitioned between NH$_4$Cl (sat., 50 mL) and ether (50 mL). The aqueous phase was extracted with ether (2(50 mL), the combined extract was dried (Na$_2$SO$_4$) and evaporated, and the residue was purified by flash chromatography (silica, hexanes:ether 20:1 (6:1) to yield recovered ketone 19 (1.71 g, 4.25 mmol) followed by the aldol product 27 in diastereomerically pure form (2.73 g, 81%). TLC R$_f$=0.34 (silica, hexanes:EtOAc 5:1); $[\alpha]_D$22−40 (c 1.0, CHCl$_3$); IR (film) $v_{max}$ 3502 (br), 2954, 2928, 2856, 1681, 1472, 1255, 1098, 836, 776 cm$^{-1}$; MALDI-FTMS m/z 699.4796 (MNa$^+$), calcd for $C_{39}H_{72}O_5Si_2Na$ 699.4816.

Alcohol 28. A solution of aldol product 27 (2.71 g, 4.0 mmol) and 2,6-lutidine (1.40 mL, 12 mmol) in CH$_2$Cl$_2$ (25 mL) was cooled to −20° C. and then TBSOTf (1.84 mL, 8.0 mmol) was added dropwise. The mixture was stirred for 1 h at −20° C. and the reaction was then quenched by the addition of NH$_4$Cl (sat., 25 mL). The mixture was warmed to 25° C., the phases were separated and the aqueous phase was extracted with CH$_2$Cl$_2$ (25 mL) and ether (25 mL). The combined organic phase was dried (Na$_2$SO$_4$) and evaporated, and the residue was filtered through a plug of silica eluting with hexane:ether 10:1. The filtrate was evaporated and the resulting crude silyl ether (3.14 g, 4.0 mmol, 99%) was dissolved in THF (40 mL). To this was added a cold (0° C.) solution of HF.pyridine complex (6.4 mL) and pyridine (18 mL) in THF (32 mL) at 0° C. (this solution was prepared by slowly adding the HF.pyridine complex to a solution of pyridine in THF at 0° C.; CAUTION! HF.pyridine is highly corrosive. The addition of HF.pyridine to the pyridine-THF solution is highly exothermic, and must be done with stirring and cooling in ice bath to prevent splashing), and the resulting solution was stirred at 25° C. for 4 hours. The mixture was diluted with EtOAc (100 mL), placed in an ice bath, and quenched by the careful addition of NaHCO$_3$ (sat., 100 mL) and as much solid NaHCO$_3$ as needed to ensure complete neutralization (CAUTION! Foaming!). The mixture was extracted with EtOAc (3(100 mL), and the combined extract was dried (Na$_2$SO$_4$) and evaporated, and the residue was purified by flash chromatography (silica, hexanes:EtOAc 5:1) to yield 28 as a colorless oil (2.40 g, 89%). TLC R$_f$=0.39 (silica, hexanes:EtOAc 5:1); $[\alpha]_D$22−26 (c 1.1, CHCl$_3$); IR (film) $v_{max}$ 3458 (br), 2929, 2856, 1693, 1472, 1462, 1255, 1093, 986, 836, 775 cm$^{-1}$; MALDI-FTMS m/z 699.4807 (MNa$^+$), calcd for $C_{39}H_{72}O_5Si_2Na$ 699.4816.

Ester 29: The alcohol 28 (2.40 g, 3.5 mmol), Dess-Martin period inane (3.75 g, 8.8 mmol), NaHCO$_3$ (0.74 g, 8.8 mmol) and water (76 µL, 4.2 mmol) were mixed in CH$_2$Cl$_2$ (80 mL), and the resulting suspension was stirred for 1 hour. The mixture was diluted with ether (200 mL), water (100 mL) and NaHCO$_3$ (sat., 100 mL), and was then filtered. The phases were separated and the aqueous phase was extracted with ether (2(100 mL). The combined extract was dried (Na$_2$SO$_4$) and evaporated, and the residue was filtered through a plug of silica eluting with hexanes:EtOAc 6:1. The filtrate was evaporated and the resulting crude aldehyde (2.15 g, 3.2 mmol, 90%) was dissolved in a mixture of THF (80 mL), t-BuOH (145 mL) and 2-methyl-2-butene (25 mL). To this solution was added a solution of NaH$_2$PO$_4$ (0.95 g, 6.7 mmol) and NaClO$_2$ (1.14 g, 10 mmol) in water (31 mL), and the resulting mixture was stirred vigorously for 1 hour. The volatiles were removed by evaporation, and the residue was partitioned between EtOAc (100 mL) and brine (100 mL). The phases were separated and the aqueous phase was extracted with EtOAc (3(100 mL). The combined extract was dried (Na$_2$SO$_4$) and evaporated, and the residue was dissolved in DMF (5 mL) and evaporated again to remove traces of t-BuOH. The so obtained crude acid (2.4 g, ca. 3.2 mmol>100%,) was again dissolved in DMF (10 mL), to which 2-(trimethylsilyl)ethanol (1.83 mL, 12.7 mmol), EDC (0.92 g, 4.8 mmol), and 4-DMAP (40 mg, 0.33 mmol) were added. The resulting suspension was stirred for 14 hours, after which time a clear solution was obtained. Water (10 mL) was added and the mixture was extracted with ether (3(50 mL). The combined extract was washed with water-brine mixture (100+100 mL), dried (Na$_2$SO$_4$) and evaporated. The residue was purified by flash chromatography (silica, hexanes:EtOAc 10:1) to yield ester 29 as a viscous, pale yellow oil (2.08 g, 74%). TLC R$_f$=0.57 (silica, hexanes:EtOAc 10:1); [α]$_D$22-33 (c 1.2, CHCl$_3$); IR (film) v$_{max}$ 2954, 2930, 2856, 1735, 1695, 1472, 1385, 1252, 1090, 988, 836, 776 cm$^{-1}$; MALDI-FTMS m/z 813.5315 (MNa$^+$), calcd for C$_{44}$H$_{82}$O$_6$Si$_3$Na 813.5311.

Aldehyde 30. To a solution of benzyl ether 29 (2.08 g, 2.63 mmol) in EtOH:EtOAc 1:1 (50 mL) was added 20% Pd(OH)$_2$ on carbon (2.1 g, 60% moisture), and the mixture was hydrogenated for 1 hour. It was then filtered through celite to remove the catalyst, the filtrate was evaporated, and the residue was co-evaporated with benzene to remove traces of EtOH. The resulting crude alcohol (1.89 g, ca. 2.6 mmol, >100%) was dissolved in CH$_2$Cl$_2$ (60 mL), Dess-Martin periodinane (2.76 g, 6.5 mmol), NaHCO$_3$ (0.55 g, 6.5 mmol) and water (56 µL, 3.1 mmol) were added, and the resulting suspension was stirred for 1 hour. The mixture was diluted with ether (150 mL), water (75 mL) and NaHCO$_3$ (sat., 75 mL), and was then filtered. The phases were separated and the aqueous phase was extracted with ether (2(75 mL). The combined extract was dried (Na$_2$SO$_4$) and evaporated, and the residue was purified by flash chromatography (silica, hexanes:EtOAc 15:1) to yield aldehyde 30 as a viscous oil (1.55 g, 84%). TLC R$_f$=0.24 (silica, hexanes:EtOAc 15:1); [α]$_D$22-47 (c 1.3, CHCl$_3$); IR (film) v$_{max}$ 2954, 2856, 1734, 1703, 1251, 1173, 1084, 988, 837, 776 cm$^{-1}$; MALDI-FTMS m/z 721.4671 (MNa$^+$), calcd for C$_{37}$H$_{74}$O$_6$Si$_3$Na 721.4685.

Enol ether 31. To a suspension of MeOCH$_2$PPh$_3$Cl (3.09 g, 9.0 mmol) in THF (20 mL) at 0° C. was added NaHMDS (8.5 mL, 8.5 mmol, 1 M in THF) dropwise. A red color developed. The mixture was stirred at 0° C. for 0.5 h and it was then cooled to –40° C. A solution of aldehyde 30 (2.12 g, 3.0 mmol) in THF (7 mL) was added, and the mixture was allowed to warm to –10° C. over 2 hours. The reaction was quenched with NH$_4$Cl (sat., 15 mL), the phases were separated, and the aqueous phase was extracted with EtOAc (2(75 mL). The combined extract was dried (Na$_2$SO$_4$) and evaporated, and the residue was purified by flash chromatography (silica, hexanes:EtOAc 30:1) to yield enol ether 31 as a colorless, viscous oil (1.85 g, 84%, olefin cis:trans ca. 1:1 by $^1$H NMR). TLC R$_f$=0.23 (silica, hexanes:EtOAc 30:1); [α]$_D$22-36 (c 1.2, CHCl$_3$); IR (film) v$_{max}$ 2954, 2930, 2856, 1735, 1695, 1251, 1171, 1105, 988, 836, 776 cm$^{-1}$; MALDI-FTMS m/z 749.4996 (MNa$^+$), calcd for C$_{39}$H$_{78}$O$_6$Si$_3$Na 749.4998.

Aldehyde 32. To a solution of enol ether 31 (847 mg, 1.16 mmol) in dioxane:water 9:1 (12 mL) was added pyridinium para-toluenesulfonate (2.34 g, 9.31 mmol) and the mixture was stirred at 70° C. until TLC indicated the completion of the reaction (6–10 h). The reaction was then quenched with NaHCO$_3$ (sat., 15 mL), and the mixture was extracted with EtOAc (3(50 mL). The combined extract was dried (Na$_2$SO$_4$) and evaporated, and the residue was purified by flash chromatography (silica, hexanes:EtOAc 15:1) to yield 32 as a colorless, viscous oil (681 mg, 82%). TLC R$_f$=0.29 (silica, hexanes:EtOAc 15:1); [α]$_D$22-34 (c 1.0, CHCl$_3$); IR (film) v$_{max}$ 2954, 2856, 1731, 1695, 1251, 1086, 988, 836, 776 cm$^{-1}$; MALDI-FTMS m/z 735.4823 (MNa$^+$), calcd for C$_{38}$H$_{76}$O$_6$Si$_3$Na 735.4842.

Construction of Vinyl Iodides 20c–g

2-Brom-5-[(trityloxy)methyl]pyridine 34. Trityl chloride (3.90 g, 14 mmol), 4-DMAP (2.08 g, 17 mmol) and 2-bromo-5-hydroxymethylpyridine 33 (1.88 g, 10 mmol) (Ellingboe, J. W., et al., J. Med. Chem. 1994, 37, 542–550) were dissolved in DMF (15 mL) and the solution was stirred at 80° C. for 48 hours. A white precipitate formed during this time. After cooling, the mixture was diluted with NaHCO$_3$ (sat., 25 mL) and extracted with EtOAc (3(50 mL). The combined extract was washed with brine, with a few drops of NaOH (1 M) added (2(100 mL). After drying and evaporation, the solid residue was purified by flash chromatography (silica, hexanes:EtOAc 15:1) to yield 34 as a white solid (4.46 g, 100%). TLC R$_f$=0.30 (silica, hexanes:EtOAc 15:1); IR (film) v$_{max}$ 3057, 1448, 1086, 764, 700, 632 cm$^{-1}$; MALDI-FTMS m/z 430.0792 (MH$^+$), calcd for C$_{25}$H$_{21}$BrNO 430.0801.

Sonogashira coupling of aryl bromdes (34, 37, 38, and 39) with propyne (general procedure). To a briefly deoxygenated (Ar bubbling) solution of the aryl bromide 34, 37, 38, or 39 (3.5 mmol) in DMF (3 mL) and diisopropyl amine (2.5 mL) were added Pd(PPh$_3$)$_2$Cl$_2$ (25 mg, 36 µmol) and CuI (13 mg, 70 µmol) under Ar(g), and then the inert atmosphere was replaced by propyne (1 atm, balloon). The mixture was stirred at 25° C. for 3 hours. During this time, a precipitate formed, and the reaction mixture turned dark brown. Water (15 mL) was added, the mixture was extracted with EtOAc, and the combined extract was dried (Na$_2$SO$_4$) and evaporated. The pure 1-arylpropyne was obtained by flash chromatography (silica, hexane:EtOAc mixtures).

Propynylpyridine 35. Brown foam (96%); TLC R$_f$=0.23 (silica, hexanes:EtOAc 5:1); IR (film) v$_{max}$ 3057, 2229, 1594, 1560, 1478, 1448, 1075, 702 cm$^{-1}$; MALDI-FTMS m/z 390.1851 (MH$^+$), calcd for C$_{28}$H$_{24}$NO 390.1852.

Pyridine 36. A solution of trityl ether 35 (1.38 g, 3.54 mmol) in CHCl$_3$ (15 mL) was cooled to 0° C. and then saturated with HCl (g). After 1 h at 0° C., the reaction was quenched by the addition of NaHCO$_3$ (sat., 50 mL), and the phases were separated. The aqueous phase was extracted with CH$_2$Cl$_2$ (50 mL) and the combined organic phase was dried (Na$_2$SO$_4$) and evaporated. Flash chromatography (silica, hexanes:EtOAc 1:2+5% MeOH) afforded 5-hydroxymethyl-2-pr p-1-ynylpyridin as a yellow, viscous oil (0.36 g, 69%). TLC R$_f$=0.29 (silica, hexanes:EtOAc 1:2+5% MeOH); IR (film) v$_{max}$ 3262, 2916, 2230, 1596, 1561, 1023, 838 cm$^{-1}$; MALDI-FTMS m/z 148.0754 (MH$^+$), calcd for C$_9$H$_{10}$NO 148.0757. To a solution of this alcohol (0.40 g, 2.7 mmol) in THF (10 mL) at 0° C. was added NaH (0.13 g, 3.3 mmol, 60% in oil). After stirring for 5 min, chloromethyl methyl ether (0.25 mL, 3.3 mmol) was added, and the mixture was stirred at 0° C. for 1 hour. The reaction was then quenched with NaCl (sat.), and a few drops of NaOH (1 M) were added. The mixture was extracted with EtOAc (3(50 mL), the combined extract was dried (Na$_2$SO$_4$) and evaporated, and the residue was purified by flash chromatography (silica, hexanes:EtOAc 1:1) to yield 36 as a pale yellow oil (0.26 g, 50%). TLC R$_f$=0.41 (silica, hexanes:EtOAc 1:1); IR (film) v$_{max}$ 2947, 2230, 1595, 1560, 1478, 1149, 1104, 1047, 919, 830 cm$^{-1}$; MALDI-FTMS m/z 192.1014 (MH$^+$), calcd for C$_{11}$H$_{14}$NO$_2$ 192.1019.

Sonogashira coupling product from 37. The reaction was very slow, probably due to Pd coordination to the thioether moiety; therefore, 10 mol % Pd(PPh$_3$)$_2$Cl$_2$ and 20 mol % CuI were used. The product was obtained as a brown oil (42%). TLC R$_f$=0.37 (silica, hexanes:EtOAc 15:1); IR (film) v$_{max}$ 3110, 2914, 2240, 1493, 1417, 1278, 1037, 966, 735 cm$^{-1}$; MALDI-FTMS m/z 170.0092 (MH$^+$), calcd for C$_7$H$_8$NS$_2$ 170.0093.

Sonogashira coupling product from 38. Brown oil (97%); TLC R$_f$=0.21 (silica, hexanes:EtOAc 5:1); IR (film) v$_{max}$ 2908, 2226, 1567, 1531, 1461, 1431, 1361, 1108, 1008, 832 cm$^{-1}$; MALDI-FTMS m/z 164.0527 (MH$^+$), calcd for C$_9$H$_{10}$NS 164.0528.

Sonogashira coupling product from 39. Yellow oil (70%); TLC R$_f$=0.36 (silica, hexanes:EtOAc 20:1); IR (film) v$_{max}$ 2924, 2231, 1566, 1554, 1431, 1156, 1140, 790 cm$^{-1}$; MALDI-FTMS m/z 164.0526 (MH$^+$), calcd for C$_9$H$_{10}$NS 164.0528.

Hydrostannylation-iodination (general procedure). This is an adaption of the previously reported procedure (Betzer, J.-F., et al., *Tetrahedron Lett.* 1997, 38, 2279–2282). To a solution of hexabutyiditin (10.1 mL, 20 mmol) in dry THF (40 mL) at −78° C. was added n-BuLi (12.9 mL, 20 mmol, 1.55 M in hexanes), and the resulting clear solution was stirred at −40° C. for 30 min. It was then transferred via cannula to a suspension of CuCN (0.90 g, 10 mmol) in THF (2 mL) at −78° C. A clear yellow solution formed, and it was stirred for 5 min at −40° C. before being re-cooled to −78° C. Then dry methanol (23 mL, 0.57 mol) was added to yield a red solution, which was stirred at −40° C. for 15 min, after which a solution of the arylpropyne (5.0 mmol) in THF (5 mL) was added. The orange-red solution was stirred at −10° C. overnight (some Cu and/or Cu$^{2+}$ salts precipitate), then cooled to −20° C., followed by the addition of methanol (10 mL). After 15 min at −20° C., water (10 mL) was added, and stirring was continued for another 15 min, while warming to 25° C. The mixture was extracted with ether, and the organic phase was washed with brine, dried (Na$_2$SO$_4$) and evaporated. Flash chromatography (silica, hexanes:EtOAc mixtures) yielded the intermediate vinylstannane, which was dissolved in CH$_2$Cl$_2$ (5 mL). A solution of iodine (1.05 equiv.) in CH$_2$Cl$_2$ (40 mL per g I$_2$) was then added dropwise to this solution at 0° C. After the last few drops, the color of I$_2$ persisted, and the reaction was allowed to continue for another 5 min at 0° C. Then the solvent was evaporated and the residue was dissolved in ether. KF (1 M solution in water, 3 equiv.) and Na$_2$S$_2$O$_3$ (sat., 10 mL per mmol substrate) were added, and the mixture was stirred for 15 min at 25° C. during which time a white precipitate formed. The mixture was filtered through celite, and the organic phase was dried (Na$_2$SO$_4$) and evaporated. The residue was purified by flash chromatography (silica, hexanes:EtOAc mixtures) to yield the desired vinyl iodide.

Vinyl iodide 20c. White cloudy film (80%). TLC R$_f$=0.25 (silica, hexanes:EtOAc 20:1); IR (film) v$_{max}$ 3060, 2919, 1619, 1596, 1484, 1443, 1373, 1214, 1061, 985, 873, 761, 703, 632 cm$^{-1}$; MALDI-FTMS m/z 518.0990 (MH$^+$), calcd for C$_{28}$H$_{25}$INO 518.0975.

Vinyl iodide 20d. Yellow oil (67%). TLC R$_f$=0.51 (silica, hexanes:EtOAc 4:1); IR (film) v$_{max}$ 2924, 1716, 1619, 1596, 1481, 1372, 1211, 1149, 1102, 1045, 918, 873, 609, 517 cm$^{-1}$; MALDI-FTMS m/z 320.0142 (MH$^+$), calcd for C$_{11}$H$_{15}$INO$_2$ 320.0142.

Vinyl iodide 20e. The intermediate vinyl stannane is readily protodestannylated; therefore, flash chromatography of this intermediate must be performed using hexanes: EtOAc:Et$_3$N 50:1:1 as eluent, and the so obtained vinylstannane contained other butyl tin compunds. Following the general procedure, the mixture was treated with enough I$_2$ that the brown color persisted at the end of the addition (ca. 2 equiv. of I$_2$). After flash chromatography (hexanes:EtOAc 50:1), vinyl iodide 20e was obtained as a yellow oil (74%). TLC R$_f$=0.41 (silica, hexanes:EtOAc 50:1); IR (film) v$_{max}$ 3102, 2923, 1620, 1423, 1300, 1065, 1035, 964, 863, 723, 562 cm$^{-1}$; MALDI-FTMS m/z 297.9215 (MH$^+$), calcd for C$_7$H$_9$INS$_2$ 297.9216.

Vinyl iodide 20f. Yellow solid (80%). TLC R$_f$=0.19 (silica, hexanes:EtOAc 40:1); IR (film) v$_{max}$ 2919, 1619, 1567, 1467, 1431, 1373, 1108, 1067, 1014, 961, 867, 820, 521 cm$^{-1}$; MALDI-FTMS m/z 291.9655 (MH$^+$), calcd for C$_9$H$_{11}$INS 291.9651.

Vinyl iodide 20g. Yellow oil (83%). TLC R$_f$=0.28 (silica, hexanes:EtOAc 40:1); IR (film) v$_{max}$ 2919, 1620, 1549, 1425, 1155, 1138, 1061, 991, 961, 861, 785, 732, 550 cm$^{-1}$; MALDI-FTMS m/z 291.9653 (MH$^+$), calcd for C$_9$H$_{11}$INS 291.9651.

Synthesis of Epothilone Analogues 8–144

Nozaki-Hiyama-Kishi coupling of aldehydes (34, 40) with vinyl stannanes (20a–g) (general procedure). To a briefly vacuum-degassed solution of aldehyde 32 (107 mg, 0.15 mmol), the requisite vinyl iodide 20 (0.45 mmol), and 4-tert-butylpyridine (665 μL, 4.5 mmol) in DMSO (3 mL) were added anhydrous CrCl$_2$ (184 mg, 1.5 mmol) and anhydrous NiCl$_2$ (4 mg, 0.03 mmol). The mixture was stirred at 25° C. for 3 hours, after which another portion of vinyl iodide (0.45 mmol) was added, and stirring was continued for a further 3 hours. This was repeated one more time, after which stirring was continued overnight. The reaction was then quenched with water (5 mL), pyridine (1 mL) was added to prevent Cr-product complexes from being extracted into the water phase, and the mixture was extracted with EtOAc (3(25 mL). The combined extract was washed with brine (2(100 mL), dried (Na$_2$SO$_4$) and evaporated. Flash chromatography (silica, hexanes:EtOAc mixtures) yielded the coupling product, in most cases inseparable from excess 4-tert-butylpyridin.

Product from 20a and 32. Yellow oil (85% as a ca. 1:1 mixture of C15 epimers). TLC R$_f$=0.26 (silica, hexanes: EtOAc 4:1); [α]$_D$22−25 (c 0.36, CH$_2$Cl$_2$); IR (film) v$_{max}$ 2943, 2860, 1731, 1696, 1467, 1384, 1290, 1249, 1173, 1079, 985, 832, 773 cm$^{-1}$; MALDI-FTMS m/z 860.5128 (MNa$^+$), calcd for C$_{44}$H$_{83}$NO$_6$SSi$_3$Na 860.5141.

Product from 20b and 32. This coupling product was inseparable from 4-tert-butyl pyridine, and was subjected to the TBAF deprotection conditions (vide infra) as a crude mixture.

Product from 20d and 32. This coupling product was inseparable from 4-tert-butyl pyridine, and was subjected to the TBAF deprotection conditions (vide infra) as a crude mixuture.

Product from 20e and 32. Yellow glass (78%, ca. 1:1 mixture of C15 epimers). TLC $R_f$=0.40 (silica, hexanes: EtOAc 5:1); $[\alpha]_D 22$–28 (c 2.0, CHCl$_3$); IR (film) $v_{max}$ 3416 (br), 2929, 2856, 1732, 1694, 1472, 1251, 1037, 988, 836, 776 cm$^{-1}$; MALDI-FTMS m/z 906.5021 (MH$^+$), calcd for $C_{45}H_{85}NO_6S_2Si_3Na$ 906.5018.

Product from 20f and 32. This coupling product was inseparable from 4-tert-butyl pyridine, and was subjected to the TBAF deprotection conditions (vide infra) as a crude mixture.

Product from 20g and 32. This coupling product was inseparable from 4-tert-butyl pyridine, and was subjected to the TBAF deprotection conditions (vide infra) as a crude mixture.

Product from 20c and 40. Yellow glass (87% for two steps from aldehyde 40 as a ca. 1:1 mixture of C15 epimers). TLC $R_f$=0.15 (silica, hexanes:EtOAc 4:1); $[\alpha]_D 22$–23 (c 0.19, CH$_2$Cl$_2$); IR (film) $v_{max}$ 2931, 2861, 1731, 1690, 1467, 1384, 1355, 1249, 1167, 1061, 985, 832, 773, 703 cm$^{-1}$; MALDI-FTMS m/z 1112.6634 (MNa$^+$), calcd for $C_{65}H_{99}NO_7Si_3Na$ 1112.6621.

Product from 20e and 40. Colorless glass (59%, ca. 1:1 mixture of C15 epimers). TLC $R_f$=0.27 (silica, hexanes: EtOAc 5:1); $[\alpha]_D 22$–28 (c 2.0, CHCl$_3$); IR (film) $v_{max}$ 3396 (br), 2928, 2855, 1734, 1693, 1472, 1251, 1037, 988, 836, 775 cm$^{-1}$; MALDI-FTMS m/z 892.4861 (MNa$^+$), calcd for $C_{44}H_{83}NO_6S_2Si_3Na$ 892.4862.

TBAF deprotection (general procedure). The product mixture from the Nozaki-Hiyama-Kishi coupling was dissolved in THF (1.5 mL), and TBAF (1 M in THF, 0.30 mL, 0.30 mmol) was added at 0° C. After 1 h at 0° C., another portion of TBAF (0.30 mL, 0.30 mmol) was added, and the mixture was stirred at 25° C. for 1 hour. The reaction was quenched with NH$_4$Cl (sat., 5 mL), and the mixture was extracted with EtOAc (4(20 mL). The combined extract was dried (Na$_2$SO$_4$) and evaporated, and the residue was purified by flash chromatography (silica, hexanes:EtOAc mixtures) to yield the desired hydroxy acid as a ca. 1:1 mixture of C15 epimers (inseparable at this stage).

Hydroxy acid 41a. The reaction mixture from the deprotection was quickly filtered through a plug of silica gel, and this crude product (73% yield from aldehyde 32) was subjected to the Yamaguchi macrolactonization (vide infra) without further purification.

Hydroxy acid 41b. Yellow solid (57%, ca. 1:1 mixture of C15 epimers). TLC $R_f$=0.19 (silica, hexanes:EtOAc 2:1); $[\alpha]_D 22$–6 (c 1.0, CHCl$_3$); IR (film) $v_{max}$ 3369 (br), 2930, 2857, 1783, 1694, 1471, 1251, 1085, 1084, 988, 836, 775 cm$^{-1}$; MALDI-FTMS m/z 768.5028 (MNa$^+$), calcd for $C_{42}H_{75}NO_6Si_2Na$ 768.5025.

Hydroxy acid 41d. Yellow glass (49% for 2 steps from aldehyde 32 as a ca. 1:1 mixture of C15 epimers). TLC $R_f$=0.20 (silica, hexanes:EtOAc 1:1); $[\alpha]_D 22$+1 (c 0.19, CH$_2$Cl$_2$); IR (film) $v_{max}$ 2933, 2858, 1694, 1600, 1563, 1463, 1382, 1357, 1251, 1145, 1096, 1046, 989, 834, 772, 666 cm$^{-1}$; MALDI-FTMS m/z 806.5437 (MH$^+$), calcd for $C_{44}H_{80}NO_8Si_2$ 806.5417.

Hydroxy acid 41e. Yellow solid (79%, ca. 1:1 mixture of C15 epimers). TLC $R_f$=0.37 (silica, hexanes:EtOAc 2:1); $[\alpha]_D 22$–23 (c 2.3, CHCl$_3$); IR (film) $v_{max}$ 3356 (br), 2929, 2856, 1712, 1472, 1253, 1085, 1038, 988, 836, 776 cm$^{-1}$; MALDI-FTMS m/z 806.4282 (MNa$^+$), calcd for $C_{40}H_{73}NO_6S_2Si_2Na$ 806.4315.

Hydroxy acid 41f. Colorless glass (63%, ca. 1:1 mixture of C15 epimers). TLC $R_f$=0.21 (silica, hexanes:EtOAc 2:1); $[\alpha]_D 22$–3 (c 0.44, CH$_2$Cl$_2$); IR (film) $v_{max}$ 2933, 2858, 1693, 1467, 1253, 1086, 984, 833, 774 cm$^{-1}$; MALDI-FTMS m/z 800.4754 (MNa$^+$), calcd for $C_{42}H_{75}NO_6SSi_2Na$ 800.4746.

Hydroxy acid 41g. Yellow glass (46% for 2 steps from aldehyde 32 as a ca. 1:1 mixture of C15 epimers). TLC $R_f$=0.46 (silica, hexanes:EtOAc 2:1); $[\alpha]_D 22$–11 (c 0.19, CH$_2$Cl$_2$); IR (film) $v_{max}$ 2933, 2858, 1706, 1557, 1463, 1426, 1364, 1251, 1083, 989, 834, 772, 666 cm$^{-1}$; MALDI-FTMS m/z 800.4746 (MNa$^+$), calcd for $C_{42}H_{75}NO_6SSi_2Na$ 800.4746.

Hydroxy acid 42c. The reaction mixture from the deprotection was quickly filtered through a plug of silica gel, and this crude product (46% yield from aldehyde 40) was subjected to the Yamaguchi macrolactonization (vide infra) without further purification.

Hydroxy acid 42e. Pale yellow glass (66%, ca. 1:1 mixture of C15 epimers). TLC $R_f$=0.39 (silica, hexanes:EtOAc 2:1); $[\alpha]_D 22$–20 (c 1.0, CHCl$_3$); IR (film) $v_{max}$ 3354 (br), 2928, 2856, 1713, 1471, 1253, 1087, 988, 836, 775 cm$^{-1}$; MALDI-FTMS m/z 792.4161 (MNa$^+$), calcd for $C_{39}H_{71}NO_6S_2Si_2Na$ 792.4153.

Yamaguchi macrolact nization (general procedure). To a solution of the hydroxy acid (95 μmol) in dry THF (8 ml) at 0° C. was added triethylamine (79 μl, 0.57 mmol) and 2,4,6-trichlorobenzoyl chloride (40 μl, 0.23 mmol). After stirring at 0° C. for 1 hour, the resulting solution was added over 2 h to a solution of 4-DMAP (26 mg, 0.21 mmol) in toluene (20 mL) at 75° C. using a syringe pump. Stirring was continued at 75° C. for another 1 h after which the toluene was evaporated under reduced pressure. The residue was directly subjected to flash chromatography (silica, hexanes:EtOAc mixtures) to yield the macrolactone and its (15R)-epimer, readily separable. In all cases the desired (15S)-epimer eluted after the less polar (15R)-epimer.

Macrolactone 43a. colorless glass (28% for two steps from the Nozaki-Hiyama-Kishi coupling product of aldehyde 32 and vinyl iodide 20a.); TLC $R_f$=0.21 (silica, hexanes:EtOAc 20:1); $[\alpha]_D 22$–33 (c 0.56, CH$_2$Cl$_2$); IR (film) $v_{max}$ 2932, 2855, 1739, 1689, 1465, 1383, 1252, 1181, 1153, 1099, 1066, 1017, 984, 869, 836, 776 cm$^{-1}$; MALDI-FTMS m/z 734.4639 (MH$^+$), calcd for $C_{40}H_{72}NO_5SSi_2$ 734.4664.

Macrolactone 43b. Colorless glass (28%); TLC $R_f$=0.27 (silica, hexanes:EtOAc 10:1); $[\alpha]_D 22$–28 (c 1.0, CHCl$_3$); IR (film) n$_{max}$ 2929, 2856, 1740, 1695, 1472, 1384, 1253, 1100, 1020, 986, 836, 775 cm$^{-1}$; MALDI-FTMS m/z 728.5109 (MH$^+$), calcd for $C_{42}H_{74}NO_5Si_2$ 728.5106.

Macrolactone 43d. Yellow glass (35%), TLC $R_f$=0.14 (silica, hexanes: EtOAc 6:1); $[\alpha]_D 22$–28 (c 0.12, CH$_2$Cl$_2$); IR (film) $v_{max}$ 2931, 2861, 1737, 1690, 1596, 1467, 1378, 1249, 1149, 1102, 1049, 985, 832, 773 cm$^{-1}$; MALDI-FTMS m/z 810.5116 (MNa$^+$), calcd for $C_{44}H_{77}NO_7Si_2Na$ 810.5130.

Macrolactone 43e. This product was isolated as a crude mixture which was directly subjected to the global desilylation conditions (vide infra) without further purification.

Macrolactone 43f. Colorless glass (45%); TLC $R_f$=0.20 (silica, hexanes:EtOAc 10:1); $[\alpha]_D 22$–0.30 (c 0.10, CH$_2$Cl$_2$); IR (film) $v_{max}$ 2933, 285, 1737, 1668, 1463, 1382, 1357, 1251, 1102, 1015, 983, 871, 834, 772 cm$^{-1}$; MALDI-FTMS m/z 760.4799 (MH$^+$), calcd for $C_{42}H_{74}NO_5SSi_2$ 760.4820.

Macrolactone 43g Yellow glass (37%); TLC $R_f$=0.47 (silica, hexanes:EtOAc 10:1); $[\alpha]_D 22$ –14 (c 0.31, CHCl$_3$); IR (film) v$_{max}$ 2929, 2856, 1740, 1696, 1557, 1461, 1431, 1379, 1250, 1099, 107, 979, 836, 774 cm$^{-1}$; MALDI-FTMS m/z 760.4802 (MH$^+$), calcd for C$_{42}$H$_{74}$NO$_5$SSi$_2$ 760.4820.

Macrolactone 44c. Colorless glass (33% for 2 steps from the Nozaki-Hiyama-Kishi coupling product of aldehyde 40 and vinyl iodide 20c); TLC $R_f$=0.46 (silica, hexanes:EtOAc 10:1); $[\alpha]_D 22$ –17 (c 0.56, CH$_2$Cl$_2$); IR (film) v$_{max}$ 2931, 2861, 1743, 1696, 1467, 1378, 1249, 1161, 1073, 1020, 985, 873, 833, 773, 703, 579 cm$^{-1}$; MALDI-FTMS m/z 972.5969 (MH$^+$), calcd for C$_{60}$H$_{86}$NO$_6$Si$_2$ 972.5988.

Macrolactone 44e. Colorless glass (47%); TLC $R_f$=0.31 (silica, hexanes:EtOAc 15:1); $[\alpha]_D 22$ –19 (c 0.50, CHCl$_3$); IR (film) v$_{max}$ 2929, 2855, 1741, 1697, 1472, 1254, 1102, 1036, 986, 836, 775 cm$^{-1}$; MALDI-FTMS m/z 774.4056 (MNa$^+$), calcd for C$_{39}$H$_{69}$NO$_5$S$_2$Si$_2$Na 774.4048.

Global desilylation (general procedure). The macrolactone was dissolved in 20% v/v TFA in CH$_2$Cl$_2$, and the solution was kept at 25° C. for 3 hours, after which the volatiles were evaporated without heating. The residue was dissolved in EtOAc, and the solution was washed with NaHCO$_3$ (sat.), dried (Na$_2$SO$_4$) and evaporated. Flash chromatography (silica, hexanes:EtOAc mixtures) afforded the pure epothilone.

Epothilone 6. Colorless glass (73%); TLC $R_f$=0.25 (silica, hexanes:EtOAc 2:1); $[\alpha]_D 22$ –34 (c 0.11, CH$_2$Cl$_2$); IR (film) v$_{max}$ 3472 (br), 2931, 1732, 1684, 1456, 1378, 1258, 1179, 1149, 1067, 1043, 1012, 973, 873, 732 cm$^{-1}$; MALDI-FTMS m/z 506.2931 (MH$^+$), calcd for C$_{28}$H$_{44}$NO$_5$S 506.2935.

Epothilone 8. Colorless glass (48%); TLC $R_f$=0.52 (silica, hexanes:EtOAc 1:1); $[\alpha]_D 22$ –54 (c 0.30, CHCl$_3$); IR (film) v$_{max}$ 3445 (br), 2936, 1732, 1682, 1454, 1383, 1259, 756 cm$^{-1}$; MALDI-FTMS m/z 500.3369 (MH$^+$), calcd for C$_{30}$H$_{46}$NO$_5$ 500.3376.

Epothilone 10. The general procedure failed to cleave the MOM protecting group cleanly. Therefore, this group was first removed using bromotrimethylsilane as follows: To a solution of protected epothilone 43d (11 mg, 14 μmol) in dry CH$_2$Cl$_2$ (0.4 mL) was added powdered 4 Å MS (5 mg), and the resulting mixture was cooled to –30° C. Bromotrimethylsilane (18.4 μL, 140 μmol) was added dropwise, and the mixture was stirred at –30° C. for 1 hour, after which the reaction was quenched with NaHCO$_3$ (sat.) and extracted five times with EtOAc. The combined extract was dried and evaporated, and the residue subjected to the general desilylation procedure to yield 10 as a colorless glass (56%); TLC $R_f$=0.42 (silica, hexanes:EtOAc 1:4); $[\alpha]_D 22$ –52 (c 0.12, CH$_2$Cl$_2$); IR (film) v$_{max}$ 3401 (br), 2931, 1731, 1684, 1596, 1561, 1461, 1378, 1331, 1290, 1255, 1173, 1149, 1044, 1008, 979, 879, 732 cm$^{-1}$; MALDI-FTMS m/z 516.3330 (MH$^+$), calcd for C$_{30}$H$_{46}$NO$_6$ 516.3319.

Epothilone 12. Viscous oil (17% from 41e); TLC $R_f$=0.38 (silica, hexanes:EtOAc 2:1); $[\alpha]_D 22$ –52 (c 0.50, CHCl$_3$); IR (film) v$_{max}$ 3490 (br), 2933, 1732, 1686, 1255, 1038, 756 cm$^{-1}$; MALDI-FTMS m/z 538.2666 (MH$^+$), calcd for C$_{28}$H$_{44}$NO$_5$S$_2$ 538.2655.

Epothilone 13. Colorless glass (68%); TLC $R_f$=0.57 (silica, hexanes:EtOAc 1:1); $[\alpha]_D 22$ –46 (c 0.34, CH$_2$Cl$_2$); IR (film) v$_{max}$ 3484 (br), 2932, 1731, 1684, 1469, 1367, 1255, 1150, 1044, 1009, 973, 879, 826, 732 cm$^{-1}$; MALDI-FTMS m/z 554.2915 (MNa$^+$), calcd for C$_{30}$H$_{45}$NO$_5$SNa 554.2910.

Epothilone 14. Colorless glass (48%); TLC $R_f$=0.42 (silica, hexanes:EtOAc 2:1); $[\alpha]_D 22$ –38 (c 0.34, CH$_2$Cl$_2$); IR (film) v$_{max}$ 3478 (br), 2930, 1732, 1682, 1556, 1434, 1378, 1257, 1149, 1137, 1067, 1044, 1012, 979, 785, 732 cm$^{-1}$; MALDI-FTMS m/z 532.3078 (MH$^+$), calcd for C$_{30}$H$_{45}$NO$_5$S 532.3091.

Epothilone 9. Colorless glass (54%); TLC $R_f$=0.13 (silica, hexanes:EtOAc 1:2); $[\alpha]_D 22$ –24 (c 0.14, CH$_2$Cl$_2$); IR (film) v$_{max}$ 3379, 2920, 2857, 1725, 1688, 1600, 1459, 1370, 1255, 1151, 1047, 1010, 979, 880, 734 cm$^{-1}$; MALDI-FTMS m/z 524.3004 (MNa$^+$), calcd for C$_{29}$H$_{43}$NO$_6$Na 524.2982.

Epothilone 11. Colorless glass (68%); TLC $R_f$=0.28 (silica, hexanes:EtOAc 2:1); $[\alpha]_D 22$ –26 (c 0.30, CHCl$_3$); IR (film) v$_{max}$ 3444 (br), 2925, 1731, 1693, 1454, 1258, 1037, 756 cm$^{-1}$; MALDI-FTMS m/z 546.2330 (MNa$^+$), calcd for C$_{27}$H$_{41}$NO$_5$S$_2$Na 546.2318.

Compound 104: $R_f$=0.19 (silica gel, ethyl acetate/hexanes=3/7); $[\alpha]_D^{20}$ –19.3 (c 0.14, CH$_2$Cl$_2$); IR (film): v$_{max}$ 3484 (br), 2932, 1729, 1459, 1375, 1249, 1043, 982, 733 cm$^{-1}$; $^1$H NMR (400 MHz, CDCl$_3$): δ=6.97 (s, 1 H), 6.47 (s, 1 H), 5.25 (dd, J=7.1, 5.7 Hz, 1 H), 4.04 (dd, J=8.1, 3.0 Hz, 1 H), 3.91 (dd, J=4.1, 4.1 Hz, 1 H), 3.23 (m, 1 H), 2.69 (s, 3 H), 2.52 (dd, J=14.9, 8.4 Hz, 1 H), 2.46 (dd, J=14.9, 2.6 Hz, 1 H), 2.11 (s, 3 H), 2.04 (dd, J=14.5, 4.0 Hz, 1 H), 1.66–1.72 (m, 1 H), 1.44–1.62 (m, 4 H), 1.36 (s, 3 H), 1.22–1.35 (m, 2 H), 1.17 (d, J=7.5 Hz, 3 H), 1.16 (s, 3 H), 1.04–1.15 (m, 1 H), 0.99 (d, J=7.0 Hz, 3 H), 0.97 (s, 3 H), 0.48 (m, 1 H), 0.40 (dd, J=8.8, 3.9 Hz, 1 H), –0.11 ppm (br t, J=4.6 Hz, 1 H); $^{13}$C NMR (100 MHz, CDCl$_3$): δ=221.5, 171.1, 165.7, 152.9, 138.6, 120.1, 116.2, 82.0, 73.8, 73.2, 52.0, 42.9, 39.4, 36.5, 35.0, 33.2, 31.6, 24.6, 23.5, 22.54, 22.49, 21.1, 20.8, 19.4, 17.4, 16.8, 15.0, 13.2 ppm; MALDI-FTMS: m/z 538.2632 (MH$^+$), calcd for C$_{28}$H$_{44}$NO$_5$S$_2$ 538.2655.

Compound 106: $R_f$=0.27 (silica gel, ethyl acetate/hexanes=1/1); $[\alpha]_D 20$ –61 (c 0.12, CH$_2$Cl$_2$); MALDI-FTMS: m/z 500.3376 (MH$^+$), calcd for C$_{30}$H$_{46}$NO$_5$ 500.3370.

Compound 107: $R_f$=0.37 (silica gel, ethyl acetate/hexanes=1/1); $[\alpha]_D 20$ –44 (c 0.14, CH$_2$Cl$_2$); MALDI-FTMS: m/z 554.2604 (MH$^+$), calcd for C$_{28}$H$_{44}$NO$_6$S$_2$ 554.2604.

Compound 108: $R_f$=0.31 (silica gel, ethyl acetate/hexanes=1/1); $[\alpha]_D 20$ –32 (c 0.33, CH$_2$Cl$_2$); MALDI-FTMS: m/z 608.2334 (MH$^+$), calcd for C$_{28}$H$_{41}$F$_3$NO$_6$S$_2$ 608.2322.

Compound 109: $R_f$=0.38 (silica gel, ethyl acetate/hexanes=1/1); $[\alpha]_D 20$ –43 (c 0.12, CH$_2$Cl$_2$); MALDI-FTMS: m/z 568.2777 (MH$^+$), calcd for C$_{29}$H$_{46}$NO$_6$S$_2$ 568.2761.

Compound 110: $R_f$=0.27 (silica gel, ethyl acetate/hexanes=1/1); $[\alpha]_D 20$ –28 (c 0.26, CH$_2$Cl$_2$); MALDI-FTMS: m/z 628.2376 (MNa$^+$), calcd for C$_{31}$H$_{43}$NO$_7$S$_2$Na 628.2373.

Compound 111: $R_f$=0.24 (silica gel, ethyl acetate/hexanes=1/1); $[\alpha]_D 20$ –49 (c 0.45, CH$_2$Cl$_2$); MALDI-FTMS: m/z 566.2116 (MH$^+$), calcd for C$_{28}$H$_{41}$BrNO$_6$ 566.2112.

Compound 112: $R_f$=0.36 (silica gel, ethyl acetate/hexanes=1/1); $[\alpha]_D 20$ –27 (c 0.15, CH$_2$Cl$_2$); MALDI-FTMS: m/z 544.2419 (MNa$^+$), calcd for C$_{28}$H$_{40}$ClNO$_6$Na 544.2436.

Compound 113: $R_f$=0.28 (silica gel, ethyl acetate/hexanes=1/1); $[\alpha]_D 20$ –49 (c 0.45, CH$_2$Cl$_2$); MALDI-FTMS: m/z 534.2907 (MH$^+$), calcd for C$_{29}$H$_{44}$NO$_6$S 534.2884.

Compound 114: $R_f$=0.35 (silica gel, ethyl acetate/hexanes=1/1); $[\alpha]_D 20$ –50 (c 0.62, CH$_2$Cl$_2$); MALDI-FTMS: m/z 556.2724 (MNa$^+$), calcd for C$_{29}$H$_{43}$NO$_6$SNa 556.2703.

Compound 17: $R_f$=0.37 (silica gel, ethyl acetate/hexanes=1/1); $[\alpha]_D 20$ –34 (c 0.24, CH$_2$Cl$_2$); MALDI-FTMS: m/z 556.2891 (MH$^+$), calcd for C$_{29}$H$_{41}$F$_3$NO$_6$ 556.2880.

Compound 116: $R_f$=0.34 (silica gel, ethyl acetate/hexanes=1/1); $[\alpha]_D 20$ –33 (c 0.80, CH$_2$Cl$_2$); MALDI-FTMS: m/z 535.2820 (MH$^+$), calcd for C$_{28}$H$_{43}$N$_2$O$_6$S 535.2836.

DETAILED DESCRIPTION OF FIGURES

Figure 1A:
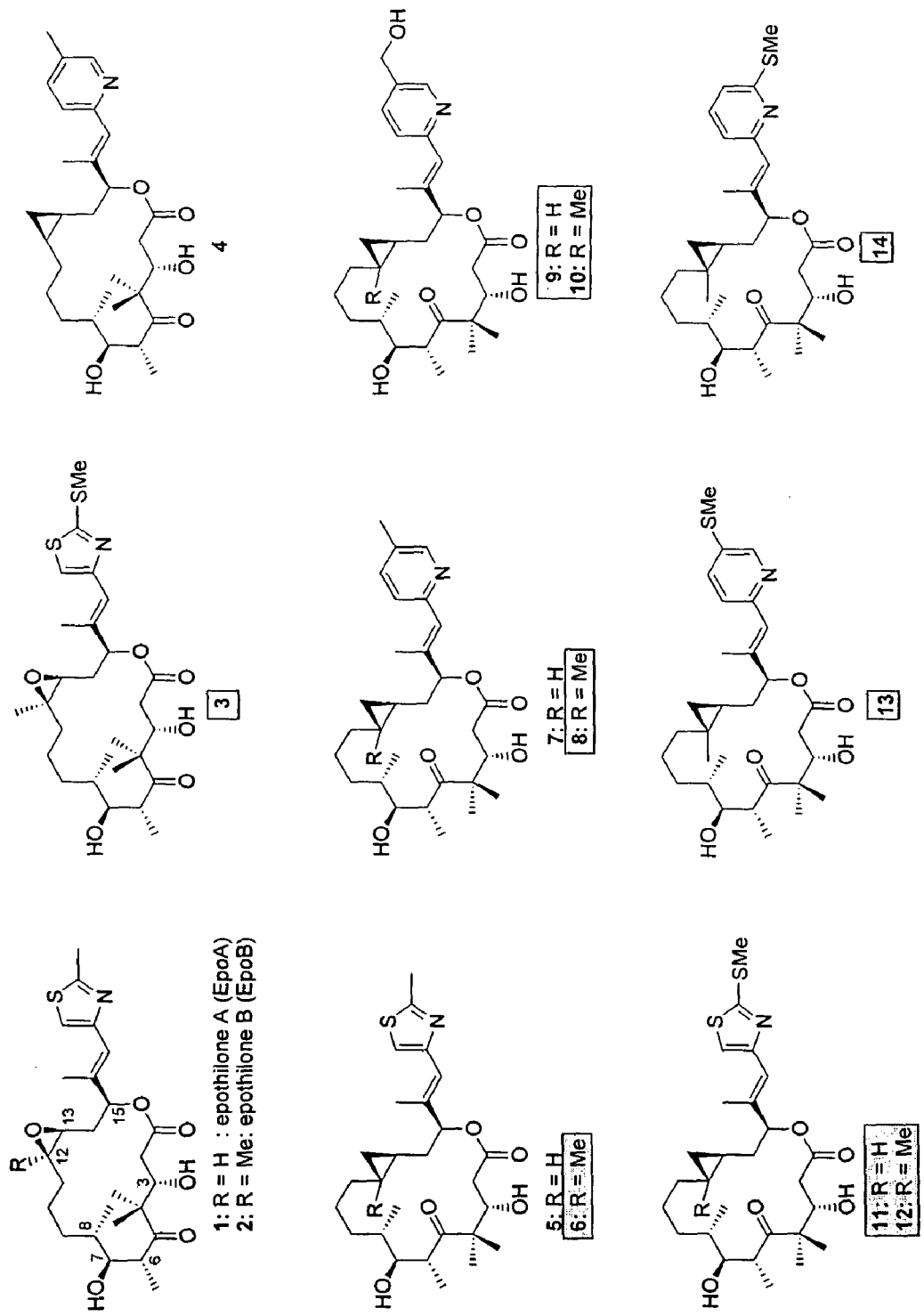
FIG. 1A illustrates the structures of selected natural and designed epothilones. Grey boxes indicate compounds synthesized in this study.
Figure 1B:
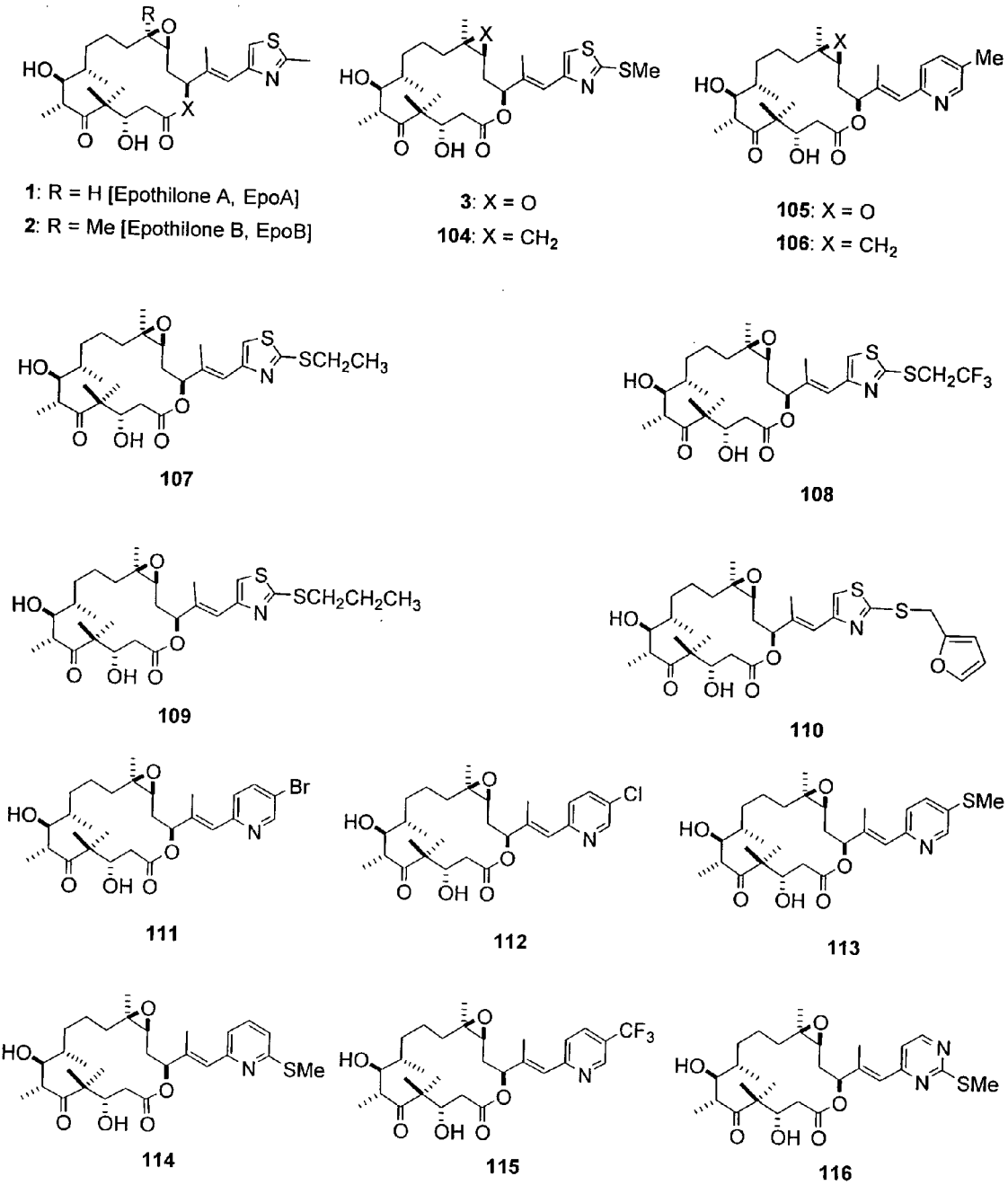
FIG. 1B illustrates a series of structures of the various designed analogs of epothilones A and B along with the structures of epothilone A and B.

FIG. 1 illustrates the structures of selected natural and designed epothilones. Grey boxes indicate compounds synthesized in this study.

FIG. 2 illustrates a chart showing the displacement of the fluorescent taxoid Flutax-2 (50 nM) from microtubule binding sites (50 nM) by competing ligands at 37° C. The dots indicate acquired data points and the lines were generated so that they give the best fit value of the binding equilibrium constant of each competitor, assuming one-to-one binding to the same site. Ligands assayed are paclitaxel (Taxol®) (dark blue), epothilone A (1) (red), epothilone B (2) (violet), compound 3 (yellow), compound 4 (light brown), and compound 8 (green). Representative curves for selected epothilone analogues (3, 4, and 8) are presented in this figure to exemplify how the binding affinities were measured for each compound in Table 3.

FIG. 3 illustrates the synthesis of 2-(thiomethyl)thiazole epothilone B (3) via Stille coupling. Reagents and conditions: $Pd_2(dba)_3 \cdot CHCl_3$ (0.2 equiv), CuI (2.0 equiv), $AsPh_3$ (0.8 equiv), DMF, 25° C., 80%. dba=dibenzylideneacetone.

FIG. 4 illustrates the retrosynthetic analysis of trans-cyclopropyl epothilone B analogues (1–6, 8, 10, 12–14).

Figure 5:
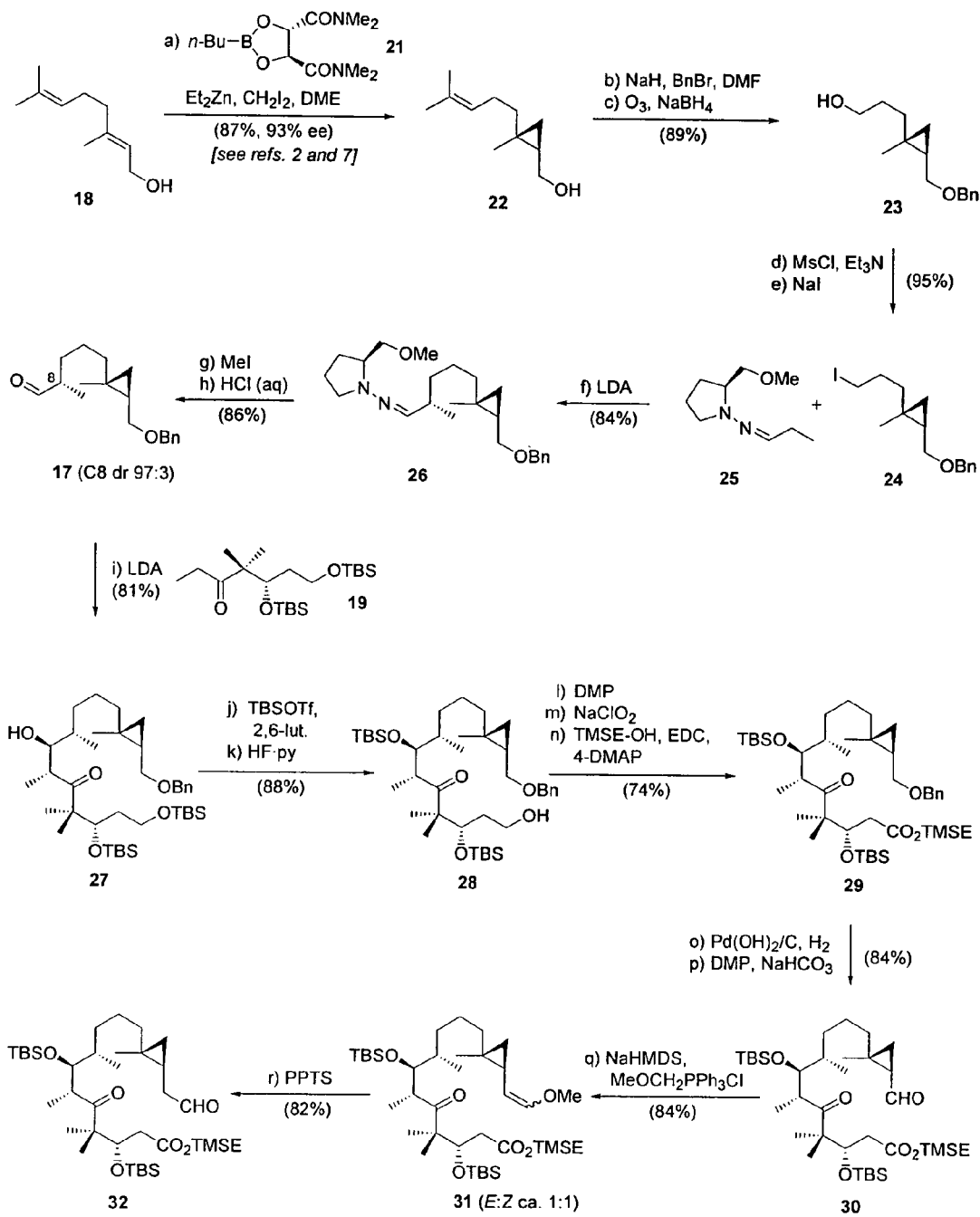
FIG. 5 illustrates the construction of aldehyde 32.

FIG. 5 illustrates the construction of aldehyde 32. Reagents and conditions: (a) See Nicolaou, K. C., et al. *ChemBioChem* 2001, 2, 69–75; Charette, A. B.; et al. *J. Am. Chem. Soc.* 1998, 120, 11943–11952; (b) NaH (1.5 equiv), BnBr (1.5 equiv), DMF, 0→25° C., 12 h; (c) $O_3$, $CH_2Cl_2$:MeOH 4:1, −78° C., 21 min; then $NaBH_4$ (3.0 equiv), −78→25° C., 1 h, 89% for 2 steps; (d) MsCl (1.3 equiv), $Et_3N$ (1.5 equiv), $CH_2Cl_2$, 25° C., 1 h; (e) NaI (3.0 equiv), acetone, reflux, 40 min, 95% for 2 steps; (f) LDA (1.4 equiv), 25 (1.3 equiv), THF, 0° C., 6 h; then 24, −98→−10° C., 14 h, 84%; (g) MeI, 60° C., 3 h; (h) 3 N HCl:pentane 1:1, 25° C., 3 h, 88% for 2 steps; (i) LDA (2.4 equiv), 19 (2.3 equiv), THF, −78° C., 1 h; then −40° C., 0.5 h; then 17 at −78° C., 5 min, 81%; (j) TBSOTf (2.0 equiv), 2,6-lutidine (3.0 equiv), $CH_2Cl_2$, −20° C., 1 h; (k) HF.py, pyridine, THF, 25° C., 4 h, 89% for 2 steps; (l) DMP (2.5 equiv), $NaHCO_3$ (2.5 equiv), $H_2O$, $CH_2Cl_2$, 25° C., 1 h; (m) $NaClO_2$ (3.1 equiv), $NaH_2PO_4$ (2.1 equiv), 2-methyl-2-butene (74 equiv), t-BuOH, THF, $H_2O$, 25° C., 1 h; (n) 2-(trimethylsilyl)ethanol (4.0 equiv), EDC (1.5 equiv), 4-DMAP (0.1 equiv), DMF, 25° C., 14 h, 74% for 3 steps; (o) 20% Pd(OH)$_2$/C, $H_2$ (1 atm), EtOH:EtOAc 1:1, 25° C., 1 h; (p) DMP (2.5 equiv), $NaHCO_3$ (2.5 equiv), $H_2O$, $CH_2Cl_2$, 25° C., 1 h, 84% for 2 steps; (q) $MeOCH_2PPh_3Cl$ (3.0 equiv), NaHMDS (2.8 equiv), THF, −40→−10° C., 2 h, 84%; (r) PPTS (8.0 equiv), dioxane: $H_2O$ 9:1, 70° C., 6 h, 82%. 4-DMAP=4-(dimethylamino)pyridine; DME=1,2-dimethoxy-ethane; DMP=Dess-Martin periodinane; EDC=1-(3-dimethylaminopropyl)-3-ethylcarbodiimide hydrochloride; HF.py=hydrogen fluoride-pyridine complex; NaHMDS=sodium hexamethyl-disilazide; PPTS=pyridinium para-toluenesulfonate; TMSE=2-trimethylsilylethyl.

Figure 6:
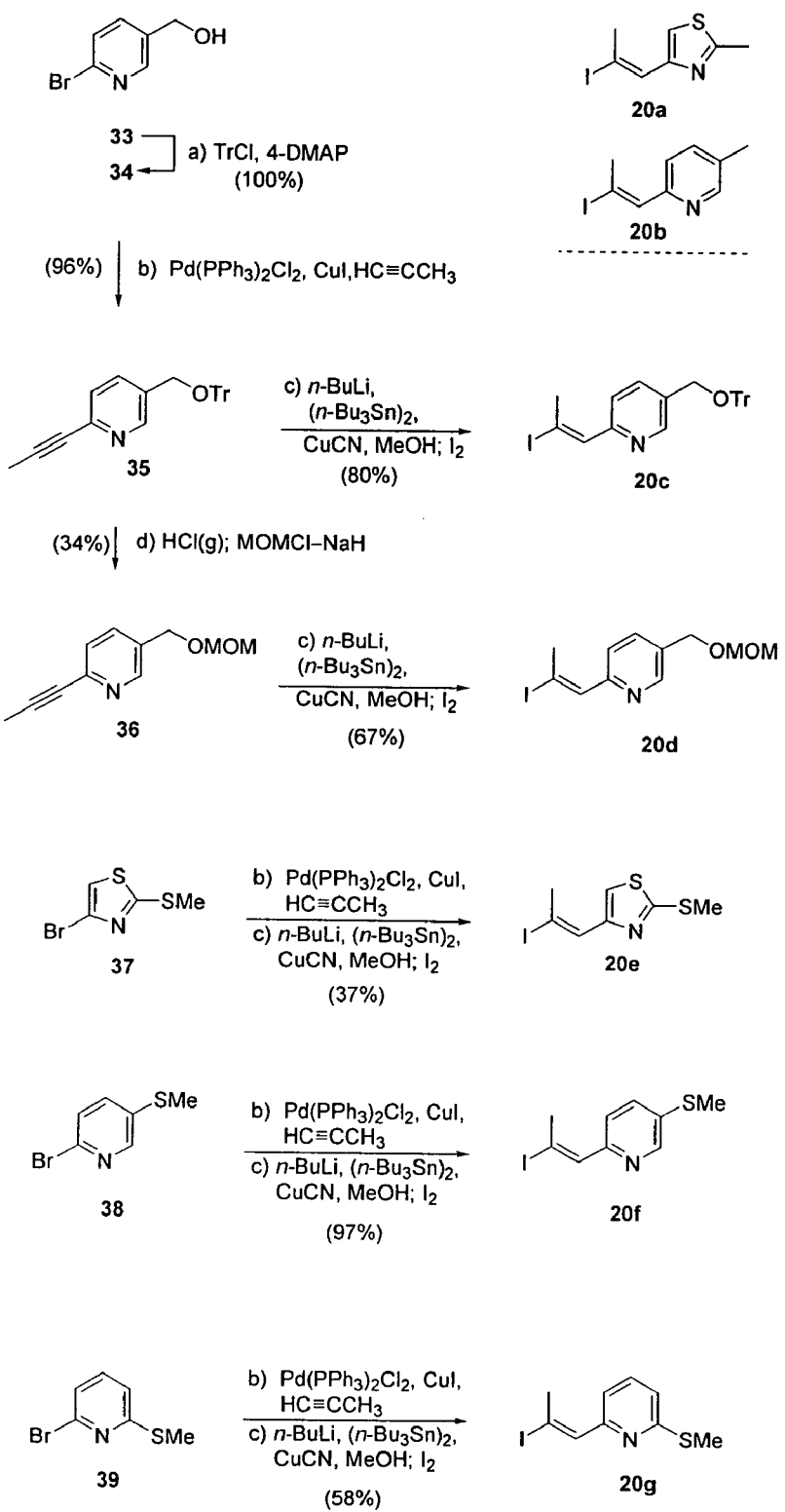
FIG. 6 illustrates the construction of vinyl iodides 20c–g.

FIG. 6 illustrates the construction of vinyl iodides 20c–g. Reagents and conditions: (a) TrCl (1.4 equiv), 4-DMAP (1.7 equiv), DMF, 80° C., 48 h, 100%; (b) Pd(PPh$_3$)$_2$Cl$_2$ (0.01 equiv), CuI (0.02 equiv), HC≡CCH$_3$ (1 atm), DMF, i-Pr$_2$NEt, 25° C., 3 h, 35: 96%; (c) (i) n-BuLi (4.0 equiv), (n-Bu$_3$Sn)$_2$ (4.0 equiv), CuCN (2.0 equiv), MeOH, THF, −10° C., 12 h; (ii) I$_2$ (1.05 equiv), CH$_2$Cl$_2$, 0° C., 5 min, 20c: 80% from 35; 20d: 67% from 36; 20e: 37% from 37; 20f: 97% from 38; 20g: 58% from 39; (d) (i) HCl(g), CHCl$_3$, 0° C., 1 h, 69%; (ii) MOMCl (1.2 equiv), NaH (1.2 equiv), THF, 0° C., 1 h, 50%. TrCl=triphenylmethyl chloride; 4-DMAP=4-(dimethylamino)pyridine; MOMCl=chloromethyl methyl ether.

Figure 7:
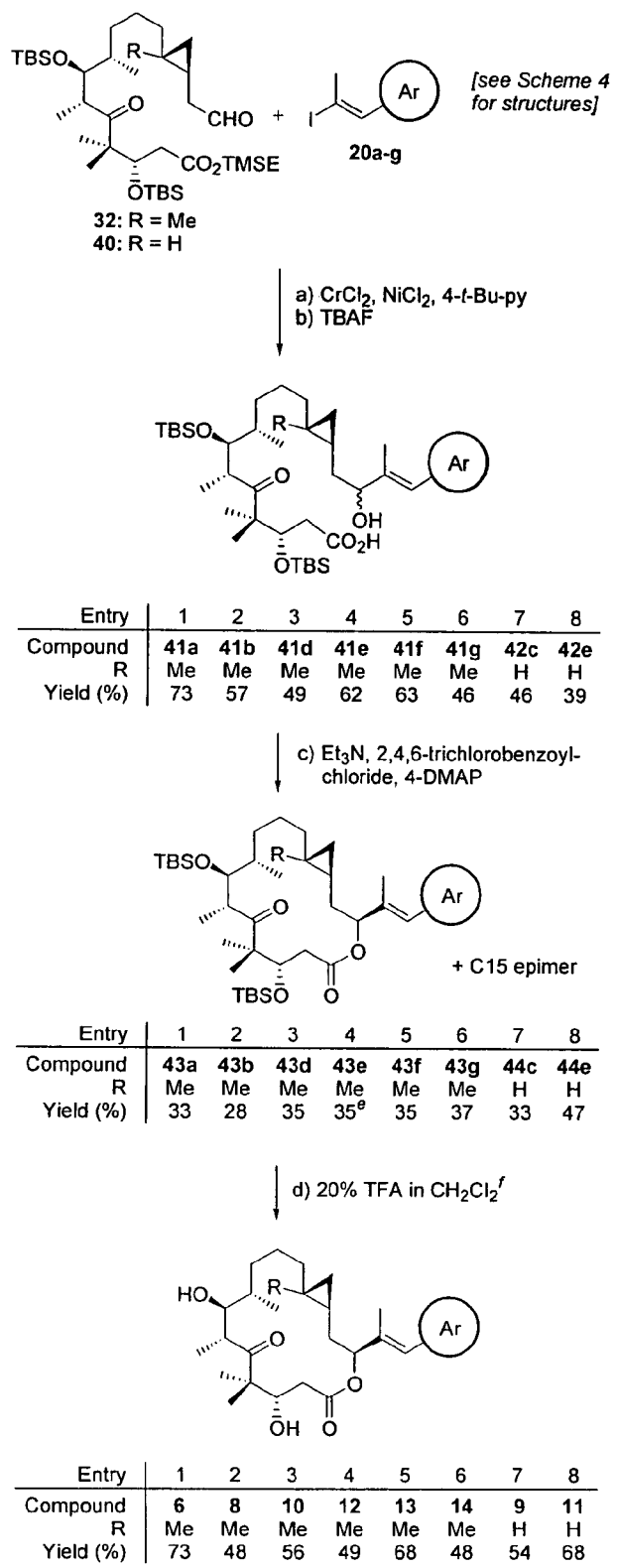
FIG. 7 illustrates the synthesis of epothilone analogues 8–14.

FIG. 7 illustrates the synthesis of epothilone analogues 8–14. Reagents and conditions: (a) CrCl$_2$ (10 equiv), NiCl$_2$ (0.2 equiv), 4-t-butylpyridine (30 equiv), 20 (3.0 equiv), DMSO, 25° C., overnight; (b) TBAF (4.0 equiv), THF, 0° C., 1 h; then 25° C., 1 h; (c) Et$_3$N (6.0 equiv), 2,4,6-trichlorobenzoylchloride (2.4 equiv), 41 or 42, THF, 0° C., 1 h; then 4-DMAP (2.2 equiv), toluene, 75° C., 3 h; (d) 20 v/v % TFA in CH$_2$Cl$_2$, 25° C., 3 h (except 43d); (e) Estimated by $^1$H NMR; (f) Deprotection of 43d: TMSBr (10 equiv), 4 Å MS, CH$_2$Cl$_2$, −30° C., 1 h; then 20 v/v % TFA in CH$_2$Cl$_2$, 25° C., 3 h. TBAF=tetrabutylammonium fluoride; 4-DMAP=4-(dimethylamino)pyridine; TFA=trifluoroacetic acid; TMSBr=trimethylsilyl bromide; MS=molecular sieves.

FIG. 8 illustrates a scheme showing the last step in the synthesis of many of the analogs from the vinyl iodide 15 and the corresponding aromatic stannanes. A Stille-type coupling of 15 with appropriate stannanes was carried out in the presence of PdCl$_2$(MeCN)$_2$, CuI and AsPh$_3$ in DMF at ambient temperature, leading directly to the analogs in the indicated yields. Reagents and conditions: a. PdCl$_2$(MeCN)$_2$ (0.5 eq), CuI (2.0 eq), AsPh$_3$ (1.0 eq), 120a–120d, 122a–122d, 123–124 (2.5 eq), DMF, 25° C., 1–3 h, 41–80%.

Figure 9:
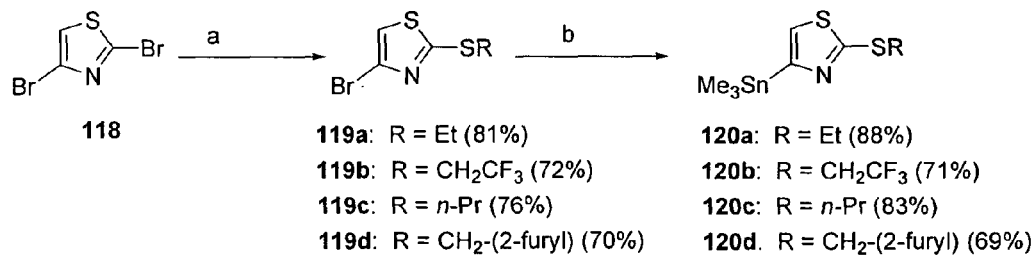
FIG. 9 illustrates a scheme showing the steps required to synthesize the stannanes used in the scheme in FIG. 8.
Figure 9:
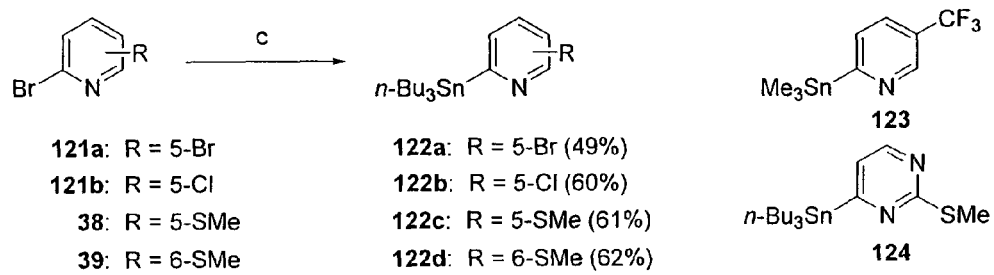

FIG. 9 illustrates a scheme showing the steps required to synthesize the stannanes used in the scheme in FIG. 8. The thiazole compounds (120a–120d) were synthesized from the commercially available 2,4-dibromothiazole (118) by reacting the corresponding thiol with NaH in the presence of the dibromothiazole. Coupling of the product with Me$_3$SnSnMe$_3$ in the presence of Pd(PPh$_3$)$_4$ in toluene at 100° C. gave the desired products 120a–120d. Reagents and conditions: a) NaH (3 eq), RSH (3 eq), i-PrOH, 24 h, 70–81%; b) (Me$_3$Sn)$_2$ (5–10 eq), Pd(PPh$_3$)$_4$ (5 mol %), toluene, 100° C., 1–3 h, 71–88%; c) n-BuLi (1.1 eq), ether, −78° C., 1 h, then n-Bu$_3$SnCl (1.2 eq), −78 to 25° C., 1 h, 49–62%.

FIG. 10 illustrates a scheme showing the synthetic route taken to build the skeleton of the cyclopropyl analogs of epothilone B. Reagents and conditions: (a) Nicolaou, K. C.; et al. *J. Am. Chem. Soc.* 2001, 123, 9313 and Jessie, S; Kjell, U. *Tetrahedron* 1994, 50, 275; (b) NaH (1.5 eq), BnBr (1.2 eq), DMF, 0 to rt, 12 h, 100%; (c) O$_3$, CH$_2$Cl$_2$, MeOH (4:1), −78° C., then NaBH$_4$ (3 eq), −78° C. to rt, 1 h, 83%; (d) MsCl (1.3 eq), Et$_3$N (1.5 eq), DCM, rt, 1 h; (e) NaI (3 eq), acetone, rt, 12 h, 91% (2 steps); (f) LDA (1.4 eq), 25 (1.3 eq), THF, 0° C., 6 h, then 129, −98 to −10° C., 14 h, 87%; (g) MeI, reflux, 3 h; (h) 3N HCl:pentane (1:1), rt, 3 h, 91% (2 steps); (i) LDA (2.4 eq), 19 (2.3 eq), THF:ether (1:1), −78° C., 1 h, then 31 40° C., 30 min, then 132 at −78° C., 5 min, 80%; (j) TBSOTf (1.5 eq), 2,6-lutidine (2 eq), DCM, −20° C., 1 h; (k) HF.py, pyridine, THF, 0° C., 8 h, 86% (2 steps); (l) (COCl)$_2$ (1.2 eq), DMSO (2.0 eq), DCM, −78° C., 5 min, then 135 (1 eq), 20 min, then Et$_3$N (3 eq), −78 to 0° C.; (m) NaClO$_2$ (5 eq), NaH$_2$PO$_4$ (3 eq), 2-methyl-2-butene (75 eq), t-BuOH, THF, H$_2$O, rt, 1 h; (n) 2-(trimethylsilyl)ethanol (4 eq), EDC (1.5 eq), DMAP (0.1 eq), DMF, rt, 12 h, 73% (3 steps); (o) 20% Pd(OH)$_2$/C, H$_2$, EtOH:EtOAc (1:1), rt, 2 h, 89%; (p) (COCl)$_2$ (1.2 eq), DMSO (2.0 eq), DCM, −78° C., 5 min, then 137 (1 eq), 20 min, then Et$_3$N (3 eq), −78 to 0° C., 99%; (q) MeOCH$_2$PPh$_3$Cl (3 eq), n-BuLi (2.8 eq), THF, 0° C., 1 h, then 138, −78 to 0° C., 2 h, 79%; (r) PPTS (10 eq), dioxane:water (9:1), 70° C., 12 h, 81%.

FIG. 11 illustrates a scheme showing the final steps used in the synthesis of cyclopropyl analogs 104 and 106. Reagents and conditions: (a) CrCl$_2$ (10 eq), NiCl$_2$(0.2 eq), 4-t-BuPy (30 eq), 20a or 20b (3 eq), DMSO, 25° C., 24 h; (b) TBAF (2 eq), THF, rt, 2 h; (c) Et₃N (6 eq), 2,4,6-trichlorobenzoyl chloride (2.4 eq), 141 or 143, THF, 0° C., 1 h, then DMAP (2.2 eq), toluene, 75° C., 3 h; (d) 20% v/v TFA in $CH_2Cl_2$, rt, 3 h.

FIG. 12 illustrates a table with the cytotoxicities of epothilones 104, 106 and 107–116 against human carcinoma cells and β-tubulin mutant cell lines selected with paclitaxel or epothilone A. The anti-proliferative effects of the tested compounds against the parental 1A9 and the paclitaxel- and epothilone-selected drug resistant clones (PTX10, PTX22 and A8, respectively) were assessed in a 72 h growth inhibition assay using the SRB (sulforhodamine-B) assay (Skehan, P.; et al. *J. Natl. Cancer. Inst.* 1990, 82, 1107–1112.). $IC_{50}$ values for each compound are given in nM and represent the mean of 3 independent experiments±standard error of the mean. Relative resistance (RR) is calculated as an $IC_{50}$ value for each resistant sub-line divided by that for the parental cell line (1A9). The results for compound 3 are taken from Nicolaou, K. C.; et al. *Tetrahedron* 2002, 58, 6413–6432.

FIG. 13 illustrates a table with the cytotoxicities ($IC_{50}$'s in nM) of selected epothilones against the human epidermoid cell lines KB-3 and KB-8511. The antiproliferative effects of the tested compounds were assessed in two human epidermoid cancer cell lines, including a parent cell line (KB-31) and a Taxol™-resistant (due to Pgp-overexpression) cell line (KB-8511). The results for Epo B and 3 were taken from Nicolaou, K. C.; et al. *Tetrahedron* 2002, 58, 6413–6432.

FIG. 14 illustrates a table disclosing the cytotoxicity of epothilones 1 through 14 and paclitaxel against 1A9 human ovarian carcinoma cells and β-tubulin mutant cell lines selected with paclitaxel or epothilone A. The anti-proliferative effects of the tested compounds against the parental 1A9 and the paclitaxel- and epothilone-selected drug-resistant clones (PTX10, PTX22 and A8, respectively) were assessed in a 72 h growth inhibition assay using the SRB (sulforhodamine-B) assay (Skehan, P.; et al. *J. Natl. Cancer Inst.* 1990, 82, 1107–1112). $IC_{50}$ values for each compound are given in nM and represent the mean of 3–9 independent experiments±standard error of the mean. Relative resistance (RR) is calculated as an $IC_{50}$ value for each resistant sub-line divided by that for the parental cell line (1A9). CP=cyclopropyl; py=5-methylpyridine side chain; pyOH=5-hydroxymethylpyridine side chain; 5tmpy=5-thiomethylpyridine side chain; 6tmpy=6-thiomethylpyridine side chain; tmt=2-thiomethyl thiazole side chain.

FIG. 15 illustrates a table disclosing the tubulin polymerization potency and cytotoxicity of epothilones 1–8, 10–14, and paclitaxel against human epidermoid cancer cell lines. (a) The extent of porcine tubulin polymerization (TP) by 4 μM compound was quantified relative to the effect of 25 μM epothilone B (which was defined as 100%) as described (Nicolaou, K. C.; et al. *Chem. Biol.* 2000, 7, 593–599). (b) Drug concentration required for maximal inhibition of cell growth ($IC_{50}$ values given in nM) was assessed after a 96 hour drug exposure by quantification of cell mass using a protein dye method as described (Meyer, T.; et al. *Int. J. Cancer* 1989, 43, 851–856). KB-31: epidermoid Taxol®-sensitive cells, KB-8511: epidermoid Taxol®-resistant cells (due to Pgp overexpression). Relative resistance (RR) was calculated by dividing the $IC_{50}$ value for the resistant cell line by that of the sensitive cell line. (c) Data from ref. 3 (% TP values for Taxol®, Epo A and Epo B were 49, 69 and 90, respectively). CP=cyclopropyl; py=5-methylpyridine side chain; pyOH=5-hydroxymethylpyridine side chain; 5tmpy=5-thiomethylpyridine side chain; 6tmpy=6-thiomethylpyridine side chain; tmt=2-thiomethyl thiazole side chain.

FIG. 16 illustrates a table disclosing binding affinities of epothilone analogues to the taxoid binding site of microtubules. (a) The binding of the different ligands to the taxoid site of microtubules was measured by the displacement of a fluorescent Taxol® derivative (Flutax-2) from its binding site (FIG. 2) (Diaz, J. F.; et al. *J. Biol. Chem.* 2000, 275, 26265–26276). The Flutax-2 displacement isotherm of each ligand was measured at least twice with a fluorescence polarization microplate reader in a modified procedure from the previous report (Andreu, J. M.; Barasoain, I. *Biochemistry* 2001, 40, 11975–11984). Cross-linked stabilized microtubules which had been stored under liquid nitrogen were employed. The binding constant of the reference ligand Flutax-2 was measured by centrifugation and fluorescence anisotropy, at each temperature (Diaz, J. F.; et al. *J. Biol. Chem.* 2000, 275, 26265–26276). The resulting reference value was 2.2 ($10^7$ $M^{-1}$ at 37° C. (b) The equilibrium dissociation constants (Kd) are given in nM. (c) The standard binding free energy changes ($DG^0_{app}$) are given in kJ $mol^{-1}$.

What is claimed is:

1. A compound represented by the following structure:

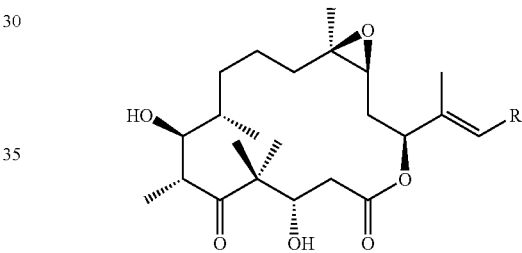

wherein R is a radical selected from the group consisting of radicals represented by the following structures:

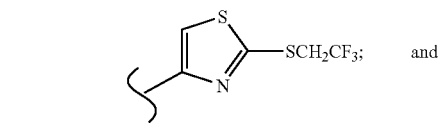
and

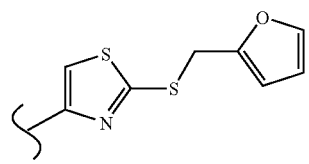

2. A compound according to claim 1 represented by the following structure:
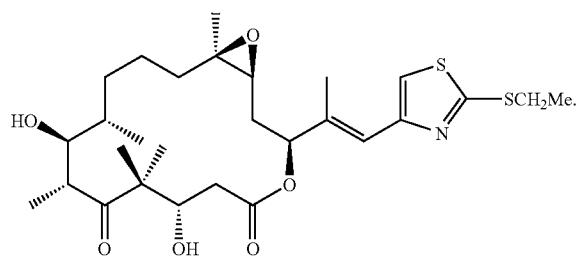
3. A compound according to claim 1 represented by the following structure:
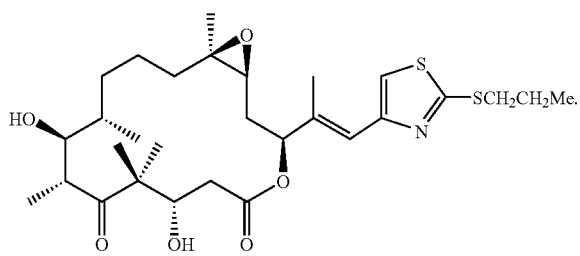
4. A compound according to claim 1 represented by the following structure:
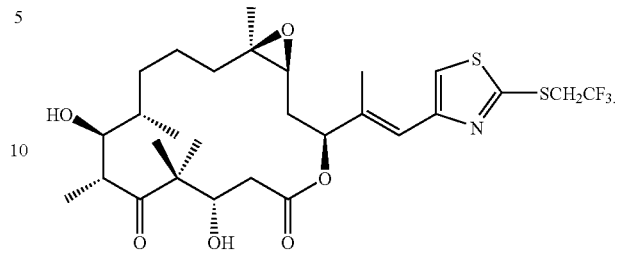
5. A compound according to claim 1 represented by the following structure:
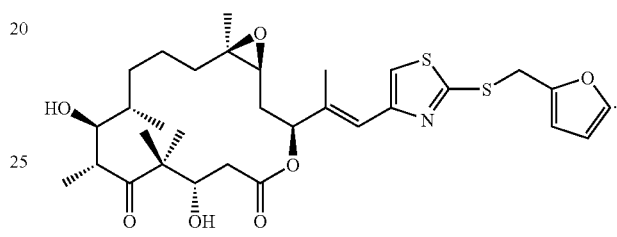
* * * * *